United States Patent [19]
Dowell et al.

[11] Patent Number: 5,384,114
[45] Date of Patent: Jan. 24, 1995

[54] OPACIFIER FOR WATER-BASED COMPOSITIONS

[75] Inventors: Teresa J. Dowell, Downers Grove; Gerald P. Newell, Hanover Park; Eugene Zeffren, Lincolnshire, all of Ill.

[73] Assignee: Helene Curtis, Inc., Chicago, Ill.

[21] Appl. No.: 97,596

[22] Filed: Jul. 23, 1993

Related U.S. Application Data

[63] Continuation of Ser. No. 859,123, Mar. 27, 1992, abandoned.

[51] Int. Cl.⁶ .................................. A61K 7/06
[52] U.S. Cl. .................... 424/70.1; 424/70.12; 424/401; 424/703; 424/702; 424/70.19; 424/70.122; 514/880; 514/188; 514/277
[58] Field of Search ........................ 424/70, 71

[56] References Cited

U.S. PATENT DOCUMENTS

| | | | |
|---|---|---|---|
| 4,275,055 | 6/1981 | Nachtigal et al. | 424/70 |
| 4,281,201 | 6/1981 | Abend | 564/506 |
| 4,472,375 | 9/1984 | Bolich, Jr. et al. | 424/70 |
| 4,548,810 | 10/1985 | Zofchak | 424/59 |
| 4,704,272 | 11/1987 | Oh et al. | 424/70 |
| 4,728,457 | 3/1988 | Fieler et al. | 252/174.15 |
| 4,741,855 | 5/1988 | Grote et al. | 252/142 |
| 4,788,006 | 11/1988 | Bolich, Jr. et al. | 252/550 |
| 4,801,447 | 1/1989 | Gum | 424/70 |
| 4,902,499 | 2/1990 | Bolich, Jr. et al. | 424/70 |
| 4,913,828 | 4/1990 | Caswell et al. | 252/546 |
| 4,960,588 | 10/1990 | Hoshowski et al. | 424/71 |
| 5,019,375 | 5/1991 | Uick | 424/70 |
| 5,019,376 | 5/1991 | Uick | 424/70 |

FOREIGN PATENT DOCUMENTS

| | | |
|---|---|---|
| 1003345 | 9/1965 | United Kingdom . |
| WO92/00283 | 1/1992 | WIPO .......... A61K 7/00 |

OTHER PUBLICATIONS

J. M. Nikitakis, ed., *CTFA Cosmetic Ingrediate Handbook, First Ed.*, (1988), p. 75.

*Primary Examiner*—Thurman K. Page
*Assistant Examiner*—Neil Levy
*Attorney, Agent, or Firm*—Marshall, O'Toole, Gerstein, Murray & Borun

[57] ABSTRACT

An opacifier comprising an amine including at least one carbon chain of at least 16 carbon atoms or a fatty amidoamine having an alkyl group including at least about thirteen carbon atoms, and a suitable acid is disclosed. The opacifier is a salt of the long-chain amine and effectively opacifies, or pearlizes, water-based compositions, such as hair treating compositions, like shampoos, conditioners, conditioning shampoos and antidandruff shampoos; and skin treating compositions, like conditioners, moisturizers and topical medicaments.

12 Claims, No Drawings

OPACIFIER FOR WATER-BASED COMPOSITIONS

CROSS-REFERENCE TO RELATED APPLICATION

This is a continuation of U. S. application Ser. No. 07/859,123, filed Mar. 27, 1992, now abandoned.

FIELD OF THE INVENTION

The present invention is directed to an opacifier and to a method of opacifying water-based compositions, wherein the opacifier imparts pearlescence to the composition, effectively resists phase separation, and assists in suspending a waterinsoluble compound, like a hair conditioning compound or a particulate antidandruff agent, in the water-based composition. More particularly, the opacifier comprises: (i) an amine having the general structural formula (I) or (II) or (III) wherein $R_1$ is an alkyl group, straight chain or branched, including at least

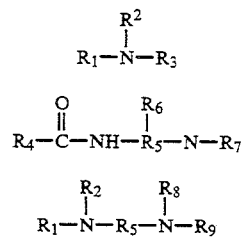

about 16 carbon atoms; $R_2$ and $R_3$ are, independently, selected from the group consisting of hydrogen, an alkyl group including from one to about 22 carbon atoms, benzyl and phenyl; $R_4$ is an alkyl group, straight chain or branched, including at least 13 carbon atoms; $R_5$ is an alkylene moiety including from one to four carbon atoms; $R_6$ and $R_7$ are, independently, an alkyl group including from one to four carbon atoms; and $R_8$ and $R_9$ are, independently, hydrogen or an alkyl group including from one to four carbon atoms, and (ii) a suitable acid selected from the group consisting of an inorganic mineral acid, an aliphatic carboxylic acid, an aromatic carboxylic acid and combinations thereof; wherein a sufficient amount of acid is included in the water-based composition such that essentially no solid particles of the amine of general structural formula (I) or (II) or (III) are present in the water-based composition. The opacifier effectively resists phase separation from the water-based composition; imparts a pearlescent effect to the water-based composition; and assists in suspending a water-insoluble insoluble compound, if present, in the water-based composition. Accordingly, the water-insoluble compound is topically delivered to the hair, scalp or skin more effectively.

BACKGROUND OF THE INVENTION

An opacifier is an ingredient included in a composition to reduce or eliminate the clear or transparent appearance of the composition. An opacifier often is included in a composition to mask an undesirable esthetic property, such as to improve the color of a composition that is darkened due to the presence of a particular ingredient, or to mask the presence of particulate matter in the composition. Opacifiers also are included in aqueous compositions to improve the esthetics and consumer acceptance of an otherwise esthetically-unacceptable composition. For example, an opacifier can impart a pearlescent appearance to a clear composition, thereby communicating an appearance of creaminess, mildness and body to the consumer. In addition, an opacifier also can impart other advantageous properties to a composition, such as thickening, suspending and emulsifying properties.

Opacifiers commonly are included in hair care compositions, such as hair shampoos, hair conditioners and combination hair shampoo-conditioners. Opacifiers also are included in skin care compositions, such as skin moisturizers, skin conditioners and topical medicaments. In general therefore, an opacifier is a compound that gives a composition either more opaque or pearlescent appearance, and does not otherwise adversely affect the composition or the usefulness of the composition.

An opacifier can be selected from a number of different chemical classes including inorganic compounds, e.g., various aluminum and magnesium salts, and organic compounds, like fatty alcohols, fatty esters and various polymers and copolymers. A representative listing of opacifiers is found in the *CTFA Cosmetic Ingredient Handbook*, J. Nikitakis, ed., The Cosmetic, Toiletry and Fragrance Association, Inc., Washington, D.C., 1988, at page 75.

The present invention is directed to a new class of opacifying compounds that impart a velvety pearlescent effect to water-based compositions, and that provide the added benefits of effectively resisting phase separation and of assisting the suspension of water-insoluble ingredients in a water-based composition. The new opacifiers are useful in topical compositions, like hair care and skin care products; in topical medicaments; and in other water-based compositions, such as cleaning compositions for hard surfaces.

While numerous compositions that include opacifiers have been disclosed, the present invention is directed to a new class of opacifying agents. Some of these previously-disclosed opacifiers are described in patents issued in the shampoo area. In particular, Oh et al., in U.S. Pat. No. 4,704,272, disclose shampoo compositions including an anionic surfactant, a nonvolatile silicone, a hair conditioning agent and a suspending agent. The hair conditioning agent can be a tri-long chain ($C_8$–$C_{22}$) amine, such as tri(isodecyl)amine or tri-$C_{13}$ amine, Oh et al. also teach that a suspending agent, like a xanthan gum or a long chain acyl derivative, is essential to the composition, and that the suspending agent may impart pearlescence to the composition. Oh et al. do not teach or suggest that a long chain amine imparts pearlescence to the product. Surprisingly, it has been found that a primary, secondary or tertiary amine including at least one carbon chain having at least sixteen carbon atoms or an amidoamine including a carbon chain having at least thirteen carbon atoms, neutralized with a suitable acid, imparts excellent pearlescence to the composition and helps provide a stable shampoo composition that effectively resist separation of the water-insoluble hair-treating compound from the shampoo compositions without the need for a separate suspending agent. Grote et al. U.S. Pat. No. 4,741,855; Oh GB Patent 2,177,108A; and Fieler et al. U.S. Pat. No. 4,728,457 similarly teach that an amine oxide or long chain acyl derivative may impart pearlescence. None of these patents teaches a long chain amine salt as an opacifier.

Bolich et al., in U.S. Pat. No. 4,472,375, disclose an aqueous hair-conditioning composition comprising a volatile hydrocarbon or a volatile silicone; a nonionic thickening agent; a quaternary ammonium salt and/or a salt of a fatty amine. The composition disclosed by Bolich et al. does not include the fatty amine salt as an opacifier. Bolich et al. do not teach or suggest the use of a fatty amine salt is an opacifier.

As will be demonstrated more fully hereinafter, an opacifier comprising: a) a fatty amine having at least one alkyl group including at least about sixteen carbon atoms or a fatty amidoamine having an alkyl group including at least about thirteen carbon atoms, and b) a suitable acid, effectively opacifies or pearlizes a water-based composition without adversely affecting the composition; effectively resists phase separation from the composition; and effectively assists in suspending a water-insoluble compound present in the water-based composition to allow a more efficient topical delivery of the water-insoluble compound to the hair, scalp or skin.

SUMMARY OF THE INVENTION

In brief, the present invention relates to an opacifier and to a method of opacifying or pearlizing water-based compositions. More particularly, the opacifier comprises: (i) an amine having the general structural formula (I) or (II) or (III), or a combination thereof, wherein $R_1$ is an alkyl group, straight chain or branched, including at least 16

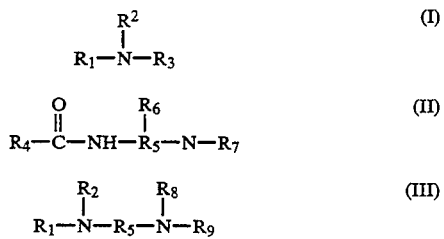

carbon atoms; $R_2$ and $R_8$ are, independently, selected from the group consisting of hydrogen, an alkyl group including from one to about 22 carbon atoms, benzyl and phenyl; $R_4$ is an alkyl group, straight chain or branched, including at least 13 carbon atoms; $R_5$ is an alkylene moiety including from one to four carbon atoms; $R_6$ and $R_7$ are, independently, an alkyl group including from one to four carbon atoms; and $R_8$ and $R_9$ are, independently, hydrogen or an alkyl group including from one to about four carbon atoms, and (ii) a suitable acid selected from the group consisting of an inorganic acid, an aliphatic carboxylic acid, an aromatic carboxylic acid and combinations thereof, wherein a sufficient amount of acid is included in the water-based composition such that essentially no solid particles of the amine of general structural formula (I) or (II) or (III) are present in the composition. An opacifier of the present invention effectively opacifies or pearlizes water-based compositions; effectively resists phase separation from the composition; demonstrates extended product stability; helps suspend a water-insoluble compound, if present, in the water-based composition to more efficiently deliver the water-insoluble compound to the hair, scalp or skin. The opacifier is especially useful in aqueous hair care compositions and in aqueous skin care compositions that include either a liquid or a particulate water-insoluble compound.

Therefore, one important aspect of the present invention is to provide an opacifier that opacifies or pearlizes a water-based composition and improved esthetic properties to the water-based composition.

Another aspect of the present invention is to provide an opacifier for a water-based composition, said opacifier comprising an amine that includes at least one alkyl group having a chain length of at least sixteen carbon atoms or an amidoamine that includes an alkyl group having a chain length of at least thirteen carbon atoms; and a sufficient amount of a suitable acid.

Another aspect of the present invention is to provide a new and improved water-based hair care composition, such as a shampoo, a conditioner, a combination shampoo/conditioner, or an antidandruff shampoo, and especially a water-based hair care composition including a water-insoluble hair treating compound, like a silicone conditioning agent or a particulate antidandruff agent. The hair care composition exhibits excellent esthetic properties and effectively resists phase separation of the water-insoluble hair treating compound due to a new opacifier comprising an amine including at least one alkyl group having at least sixteen carbon atoms or an amidoamine that includes an alkyl group having a chain length of at least thirteen carbon atoms, and a suitable acid.

Another aspect of the present invention is to provide an opacifier capable of pearlizing a water-based composition and suspending a water-insoluble compound in the water-based composition, said opacifier, comprising: (i) an amine having the general structural formula (I) or (II) or (III), wherein $R_1$ is an alkyl group, straight chain or branched, including at least 16 carbon atoms; $R_2$ and $R_3$ are, independently,

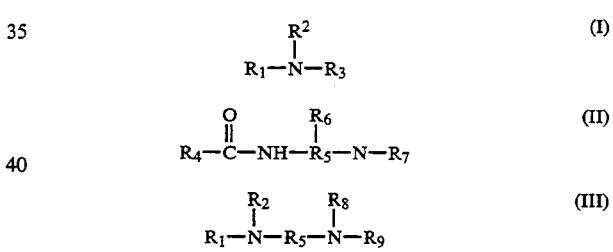

selected from the group consisting of hydrogen, an alkyl group including from one to about 22 carbon atoms, benzyl and phenyl; $R_4$ is an alkyl group, straight chain or branched, including at least 13 carbon atoms; $R_5$ is an alkylene group including from one to four carbon atoms; $R_6$ and $R_7$ are, independently, an alkyl group including from one to four carbon atoms; and $R_8$ and $R_9$ are, independently, hydrogen or an alkyl group including from one to four carbon atoms, and (ii) an inorganic acid, an aliphatic carboxylic acid, an aromatic carboxylic acid or a combination thereof; wherein a sufficient amount of acid is included in the water-based composition such that essentially no solid particles of the amine of general structural formula (I) or (II) or (III) are present.

Still another aspect of the present invention is to provide a new opacified hair care composition including 0% to about 40% of an anionic cleansing surfactant, and 0% to about 10% of a water-insoluble hair treating compound, such as a silicone conditioning compound or an antidandruff agent, wherein the hair care composition is opacified by, and the water-insoluble hair treating compound is suspended in the hair care composition by, an opacifier, said opacifier comprising: (i) from about 1% to about 10% by weight of the composition of an amine having the general structural formula (I) or (II) or (III), wherein $R_1$ is an alkyl group, straight chain or branched, including at least 16 carbon atoms;

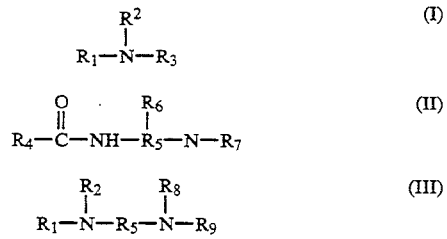

$R_2$ and $R_3$ are, independently, selected from the group consisting of hydrogen, an alkyl group including from one to about 22 carbon atoms, benzyl and phenyl; $R_4$ is an alkyl group, straight chain or branched, including at least 13 carbon atoms; $R_5$ is an alkylene group including from one to four carbon atoms; $R_6$ and $R_7$ are, independently, an alkyl group including from one to four carbon atoms; and $R_8$ and $R_9$ are, independently, hydrogen or an alkyl group including from one to four carbon atoms, and (ii) from about 0.05% to about 5% by weight of the composition of an inorganic acid, an aliphatic carboxylic acid, an aromatic carboxylic acid or a combination thereof; wherein a sufficient amount of acid is included in the hair care composition such that essentially no solid particles of the amine of general structural formula (I) or (II) or (III) are present in the composition.

Another aspect of the present invention is to provide a method of opacifying a water-based composition, such as a hair care composition or a skin care composition, by including a sufficient amount of an opacifier comprising an amine having at least one carbon chain of at least 16 carbon atoms or an amidoamine having an alkyl group including at least 13 carbon atoms, and a sufficient amount of a suitable inorganic acid, aliphatic carboxylic acid or aromatic carboxylic acid, or a combination thereof, in the composition.

The above and other aspects and advantages of the present invention will become apparent from the following detailed description of the preferred embodiments.

DETAILED DESCRIPTION OF THE PREFERRED EMBODIMENTS

An opacifier of the present invention comprises a suitable amine and a suitable acid. In accordance with an important feature of the present invention, the amine of the opacifier is an amine having the general structural formula (I) or (II) or (III):

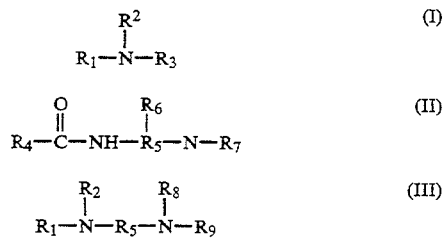

wherein $R_1$ is an alkyl group, straight chain or branched, including at least 16 carbon atoms; $R_2$ and $R_3$ are, independently, selected from the group consisting of hydrogen, an alkyl group including from one to about 22 carbon atoms, benzyl and phenyl; $R_4$ is an alkyl group, straight chain or branched, including at least 13 carbon atoms; $R_5$ is an alkylene moiety including from one to four carbon atoms; $R_6$ and $R_7$ are, independently, an alkyl group including from one to four carbon atoms; and $R_8$ and $R_9$ are, independently, hydrogen or an alkyl group including from one to four carbon atoms. In accordance with another important feature of the present invention, the acid of the opacifier is selected from the group consisting of an inorganic acid, an aliphatic carboxylic acid, an aromatic carboxylic acid or a combination thereof. The opacifier effectively opacifies, or pearlizes, water-based compositions without adversely affecting the composition; effectively resists phase separation from the composition; effectively helps suspend a water-insoluble compound, if present, in the water-based composition to more effectively deliver the water-insoluble compound to the hair, scalp or skin to impart conditioning properties, antidandruff properties or other desired hair, scalp or skin properties.

In accordance with an important feature of the present invention, an amine useful in the present invention is depicted by the general structural formula (I) or (II) or (III). The alkyl $R_9$ groups $R_1$ and $R_4$ of the amine of general structural formulas (I) or (II) or (III) can be derived from a fatty acid, and therefore do not have to be solely, or primarily, of one chain length, i.e., the long chain need not be derived only from cetyl ($C_{16}$) or stearyl ($C_{18}$). Rather, a compound of general structural formula (I) or (II) or (III) wherein the alkyl group $R_1$ or $R_4$ is a mixture of lengths can be used, as long as the amine is water insoluble and includes at least one alkyl group of sufficient chain length to impart water insolubility. Such amine compounds are prepared conveniently from naturally occurring materials, such as tallow, soya oil and the like, or from synthetically produced mixtures.

In particular, an amine of general structural formula (I) is a primary, a secondary or a tertiary amine including at least one alkyl group including at least about sixteen carbon atoms and is a solid compound at room temperature. It should be understood that a commercial amine of general structural formula (I), and having at least one carbon chain of sixteen carbon atoms as the predominant chain length, also can include a minor amount of an amine having a carbon chain of fourteen or fewer carbon atoms. A minor amount of an amine having carbon chain including less than sixteen carbon atoms, e.g., up to about 5% by weight of the amine present in the composition, does not adversely affect the opacifying ability of the opacifier. Suitable amines of general structural formula (I) are solid compounds at room temperature, and are water-insoluble compounds exhibiting a water solubility of 0.5 g (grams) or less per 100 ml (milliliters) of water.

When an amine of general structural formula (I) is sufficiently neutralized such that essentially no solid particles of the amine are present in a water-based composition, the neutralized amine opacifies the composition and forms a network that suspends a water-insoluble hair treating compound, such as a silicone conditioning agent or an antidandruff agent. The network effectively opacifies the composition and helps suspend the water-insoluble hair treating compound at least for the expected life of the product, e.g., about one year, without adversely affecting the other properties of the shampoo composition, like foam generation.

Specific primary amines of general structural formula (I) useful in a shampoo composition of the present invention include, but are not limited to, $C_{20\text{-}22}$ amine, soya amine, hydrogenated tallow amine, stearyl amine, tallow amine, oleyl amine, hexadecylamine, octadecylamine, and combinations thereof. Suitable secondary amines include, but are not limited to, di(hydrogenated tallow)amine, disoyamine, and combinations thereof. Suitable tertiary amines include, but are not limited to, tri(hydrogenated tallow) amine, di(hydrogenated tallow) methylamine, distearyl methyl amine, methyl dibehenamine, dimethyl behenamine, dimethyl tallowamine, dimethyl stearamine, dimethyl tetradecylamine, dimethyl hexadecyl amine, dimethyl octadecyl amine, dimethyl soyamine, dimethyl oleyl amine, stearyl methyl benzyl amine, dimethyl palmitamine, dimethyl (hydrogenated tallow) amine, and combinations thereof. The shampoo compositions also can include a combination of primary and/or secondary and/or tertiary amines having the structural formula (I).

As stated above, a suitable amine also can have a distribution of alkyl groups wherein the predominant alkyl group includes at least 16 carbon atoms and wherein a minor portion, such as 5% or less, of the alkyl groups include less than 16 carbon atoms. It also should be understood that a diamine of general structural formula (III) is a suitable amine. Exemplary diamines include, but are not limited to, hydrogenated tallow diamine, tallow diamine, soya diamine or oleyl diamine, having the structural formula (IV):

$$R_1NH(CH_2)_nNH_2, \qquad\qquad (IV)$$

wherein n is a number 1 through 4 and $R_1$ is an alkyl group including at least sixteen carbon atoms. The compounds depicted by structural formula (IV) also have been termed N-alkyl alkylene diamines.

In addition to an amine of general structural formula (I) or (III), an amine of general structural formula (II) also can be included in the composition as the amine, either alone or in combination with an amine of general structural formula (I) or (III). A useful amine of general structural formula (II), generally termed an amidoamine is a water-insoluble compound having a water solubility of 0.5 g or less per 100 ml of water. Examples of an amine of general structural formula (II) include, but are not limited to, stearamidopropyl diethylamine, stearamidoethyl diethylamine, stearamidoethyldimethylamine, palmitamidopropyl dimethylamine, behenamidopropyl dimethylamine, myristamidopropyl dimethylamine, oleamidopropyl dimethylamine, ricinoleamidopropyl dimethylamine, stearamidopropyl dimethylamine, and combinations thereof.

In addition to an amine having the general structural formula (I) or (II)or (III), the opacifier of the present invention also includes a suitable acid. To provide an opacifier that opacifies or pearlizes and that helps suspend a water-insoluble hair treating compound in the shampoo composition, a sufficient amount of an inorganic mineral acid or an organic carboxylic acid, either aliphatic or aromatic, is included in the composition such that essentially no solid particles of the amine are present in the composition. Accordingly, the acid used to neutralize the amine compound is of sufficient acid strength to neutralize a free amine nitrogen. Such acids include, but are not limited to, the inorganic mineral acids, like hydrochloric acid, sulfuric acid, nitric acid, phosphoric acid, and combinations thereof.

It also has been found that an aliphatic carboxylic acid including up to about 22 carbon atoms, or an aromatic carboxylic acid, can be used to neutralize the amine of general structural formula (I) or (II) or (III). Preferably, the aliphatic carboxylic acid is a saturated aliphatic acid and includes up to about 12 carbon atoms. An aliphatic carboxylic acid including more than about 12 carbon atoms, or including an olefinic unsaturation, is useful in the present composition, but provides a composition having somewhat decreased esthetic properties compared to compositions including a saturated acid having about 12 or fewer carbon atoms. Therefore, examples of suitable aliphatic carboxylic acids include, but are not limited to, acetic acid, lactic acid, citric acid, tartaric acid, propionic acid, butyric acid, pentanoic acid, glycolic acid, decanoic acid, lauric acid, octanoic acid, and combinations thereof. Oleic acid and stearic acid are nonlimiting examples of acids including more than 12 carbon atoms and/or an olefinic unsaturation that are useful in the present invention.

Examples of suitable aromatic carboxylic acids include, but are not limited to, benzoic acid, toluic acid, phthalic acid, isophthalic acid, terephthalic acid, salicylic acid, and combinations thereof. Alkyl-substituted aromatic acids also are useful in a composition of the present invention. An aliphatic carboxylic acid, aromatic carboxylic acid or mineral acid can be the sole acid included in the shampoo composition, or any combination of the three types of acid can be included in the composition. In general, a sufficient amount of acid is added to the composition such that essentially no solid particles of the amine are present in the composition and to adjust the final pH of the shampoo composition. An excess amount of acid does not adversely affect the opacifier or the water-based composition.

The opacifier of the present invention is useful in pearlizing water-based compositions, and especially water-based hair care and skin care compositions. The present invention is especially useful in water-based compositions that include a water-insoluble compound because the opacifier helps suspend the water-insoluble compound in the composition without thickening the composition to a viscosity that is unacceptable to consumers, and without adversely affecting composition performance, such as decreasing the foam generating properties of a hair shampoo. Therefore, the opacifier helps maintain the water-insoluble compound homogeneously dispersed throughout the composition for at least the expected life of the product, and does not adversely affect the foaming, cleansing, conditioning, antidandruff or other hair desirable properties of the composition.

Although the primary function of the opacifier is to pearlize the composition, when the opacifier is present in a sufficient amount, the opacifier suspends a water-insoluble compound in the water-based composition. Many conventional suspending agents operate on the principle of thickening the composition to a sufficient viscosity to retard settling or separation of the water-insoluble compound to such an extent that the composition is stable over its lifetime. However, considering the relatively high percentage of water-insoluble compound included in compositions such as conditioning and antidandruff shampoos, a suspending agent that relies only on thickening often is incorporated into the composition in such a high percentage that an unacceptably viscous product results. Compositions having such a high viscosity are not acceptable to consumers because the compositions are difficult to dispense, difficult to distribute evenly on the hair and scalp, and often do not generate an adequate foam.

A composition including an opacifier of the present invention, comprising an amine having the general structural formula (I) or (II) or (III) and a suitable acid, does not rely merely on thickening to suspend the water-insoluble compound. Generally, to both opacify or pearlize a water-based composition, and to assist in suspending a water-insoluble compounds in the water-based composition, the amine is present in an amount of about 1% to about 10%, and preferably about 1.5% to about 5%, by weight of the composition; the acid is present in a sufficient amount such that essentially no solid particles of the amine are present in the composition. Therefore, the acid is included in an amount of about 0.05% to about 5%, and preferably about 0.2% to about 3%, by weight of the composition.

In accordance with one important embodiment of the present invention, the opacifier is included in a hair care composition including either a cleansing surfactant or water-insoluble hair treating compound, or a combination thereof, and a carrier comprising water. The water-insoluble hair treating compound can be, for example, a water-insoluble hair conditioning compound, like a silicone or a hydrocarbon conditioning agent, or an antidandruff agent.

The cleansing surfactant used in the water-based composition pearlized by the opacifier of the present invention includes any of the surfactants known or previously used in the art of hair shampoos. An anionic cleansing surfactant is the preferred cleansing surfactant in this embodiment because it effectively cleanses the hair and generates a high, stable, foam level that consumers equate with cleaning efficiency. Nonionic and amphoteric surfactants generally are not as effective in cleansing the hair and do not provide the high foam level desired by consumers, but such surfactants impart mildness to the composition. Nonionic or amphoteric surfactants also can be included in a shampoo composition of this embodiment to help increase and stabilize foam, to provide a suitable viscosity, or to furnish other functional or esthetic properties to the composition. Therefore, nonionic and amphoteric surfactants can be used as the primary cleansing surfactant in the hair shampoo, but usually are included in conjunction with an anionic cleansing surfactant.

Usually, the anionic cleansing surfactant includes a hydrophobic moiety, such as a carbon chain including from about eight carbon atoms to about 30 carbon atoms, and particularly from about twelve carbon atoms to about twenty carbon atoms; and further includes a hydrophilic moiety, such as sulfate, sulfonate, carbonate, phosphate or carboxylate. Often, the hydrophobic carbon chain is etherified, such as with ethylene oxide or propylene oxide, to impart a particular physical property, such as increased water solubility or reduced surface tension, to the anionic cleansing surfactant.

The anionic cleansing surfactants are well-known and have been widely used in the art of hair shampoos. Therefore, suitable anionic cleansing surfactants include, but are not limited to, compounds in the classes known as alkyl sulfates, alkyl ether sulfates, alkyl ether sulfonates, sulfate esters of an alkylphenoxy polyoxyethylene ethanol, alpha-olefin sulfonates, beta-alkyloxy alkane sulfonates, alkyl arylsulfonates, alkyl carbonates, alkyl ether carboxylates, fatty acids, sulfosuccinates, sarcosinates, octoxynol phosphates, nonoxynol phosphates, taurates, fatty taurides, sulfated monoglycerides, fatty acid amido polyoxyethylene sulfates and isothienates; or combinations thereof. Many additional anionic cleansing surfactants are described in McCUTCHEON'S, DETERGENTS AND EMULSIFIERS, 1989 ANNUAL, published by McCutcheon Division, MC Publishing Co., and incorporated herein by reference.

Usually, the anionic cleansing surfactant is present in the composition as a neutralized salt in the form of a sodium, potassium, lithium, ammonium, alkylammonium or hydroxyalkylammonium salt, wherein the alkyl moiety includes from one to about three carbon atoms. The alkyl sulfates and alkyl ether sulfates are particularly effective classes of anionic cleansing surfactants. Consequently, exemplary anionic cleansing surfactants that are useful in the composition and method of the present invention include, but are not limited to, the ammonium, monoethanolamine, diethanolamine, triethanolamine, isopropylamine, sodium, potassium, lithium or magnesium salt of lauryl sulfate, dodecylbenzenesulfonate, lauryl sulfosuccinate, lauryl ether sulfate, lauryl ether carboxylate, lauryl sarcosinate, cocomethyl tauride, and sulfosuccinate half ester amide; or combinations thereof. An example of an especially useful anionic cleansing surfactant is a combination of a lauryl sulfate salt and a lauryl ether sulfate salt.

In place of, or in conjunction with, the anionic surfactant, an amphoteric surfactant can be included in the composition. An amphoteric surfactant enhances skin mildness and composition esthetics to improve consumer acceptance. Suitable classes of amphoteric surfactants included in the pearlized shampoo composition include, but are not limited to, betaines, hydroxypropylsultaines, amine oxides and combinations thereof. Examples of specific amphoteric surfactants include, but are not limited to, cocamidopropyl betaine, lauramidopropyl betaine, coco/oleamidopropyl betaine, coco betaine, oleyl betaine, cocamidopropyl hydroxysultaine, tallowamidopropyl hydroxysultaine and dihydroxyethyl tallow glycinate, or combinations thereof. In general, however, any amphoteric surfactant can be included in a shampoo composition pearlized by an opacifier of the present invention.

The pearlized shampoo compositions of the present invention also can include nonionic surfactants to help impart esthetic, physical or cleansing properties to the shampoo composition. Representative nonionic surfactants that can be included in a shampoo composition pearlized by an opacifier of the present invention include ethers of polyols and sugars; fatty acid alkanolamides; polyethylene glycols; the ethoxylated or propoxylated alkylphenols; ethoxylated or propoxylated fatty alcohols; and the condensation products of ethylene oxide with long chain amides. These nonionic surfactants, as well as numerous others in the art and are fully described in the literature, such as McCUTCHEON'S, DETERGENTS AND EMULSIFIERS, 1989 Annual, published by McCutcheon Division, MC Publishing Co.

In particular, a nonionic alkanolamide can be included in the composition to provide composition thickening and foam stability. The alkanolamide can be included in the pearlized shampoo composition in an amount of 0% up to about 5% by weight of the composition. Accordingly, suitable alkanolamides include, but are not limited to, those known in the art of hair care formulations, such as cocamide MEA, cocamide DEA, soyamide DEA, lauramide DEA, oleamide MIPA, stearamide MEA, myristamide MEA, lauramide MEA, capramide DEA, ricinoleamide DEA, myristamide DEA, stearamide DEA, oleylamide DEA, tallowamide DEA, lauramide MIPA, tallowamide MEA, isostearamide DEA, isostearamide MEA and combinations thereof.

The anionic, amphoteric or nonionic surfactant, or combinations thereof, is present in the hair care composition in an amount of 0% to about 40%, and preferably about 5% to about 30%, by weight of the composition. It has been found that if the cleansing surfactant is present in an amount of less than 3% by weight of the composition, then the hair is not sufficiently cleansed when contacted with the shampoo composition. To achieve the full advantage of the present invention, the cleansing surfactant generally is included in the hair shampoo composition in an amount of about 10% to about 25% by weight of the composition. Furthermore, surprisingly and unexpectedly, even when a low amount of cleansing surfactant is included in the composition, such as from about 5% to about 10% by weight of the composition, the presence of the water-insoluble hair treating compound and the amine of the opacifier do not adversely affect the generation of a sufficient and stable foam level for consumer acceptance.

In accordance with another important feature of the shampoo of this embodiment, the hair care composition includes a water-insoluble hair treating compound that imparts conditioning properties to the hair, imparts antidandruff properties to the hair or scalp. Other classes of water-insoluble hair treating compounds, in addition to hair conditioners and antidandruff agents, that are useful in the pearlized shampoo composition include, but are not limited to, hair colorants and hair fixatives. In general, the hair shampoo composition includes 0% to about 10%, and preferably about 0.5% to about 5% of the water-insoluble hair treating compound.

In one important embodiment, the shampoo composition is a shampoo/conditioner wherein the water-insoluble hair treating compound is a silicone conditioning agent, a hydrocarbon conditioning agent, a water-insoluble fatty alcohol including about 12 to about 22 carbon atoms, water-insoluble fatty ester including about 9 to about 34 carbon atoms, or other water-insoluble conditioning agent. In particular, the silicone conditioning agent can be a polyalkyl siloxane, a polyaryl siloxane or a polyalkylaryl siloxane. Mixtures of these silicone conditioning agents also can be used.

In one embodiment, the silicone conditioning agent is a nonvolatile silicone conditioning agent, like a polydimethylsiloxane compound, such as a mixture, in about a 2:1 weight ratio, of a low molecular weight polydimethylsiloxane fluid and a higher molecular weight polydimethylsiloxane gum. Preferred silicone gums include linear and branched polydimethylsiloxanes of the following general formula:

(CH$_3$)$_3$SiO—[Si(CH$_3$)$_2$O]$_n$—Si(CH$_3$)$_3$, wherein n is a number from about 2,000 to about 15,000, and preferably from about 2,000 to about 7,000. Silicone gums useful in compositions of this embodiment are available from numerous commercial sources, including General Electric Company, Waterford, N.Y., and Dow Corning Corp., Midland, Mich.

The nonvolatile polydimethylsiloxane agent is added to the composition in an amount sufficient to impart improved combing and improved feel, such as softness, to the hair after shampooing. As referred to herein, the nonvolatile polydimethylsiloxane compounds are nonfunctionalized siloxanes having a viscosity of from about 5 to about 600,000 cs (centistoke), and preferably from about 350 to about 10,000 cs, at 25° C. The so-called "rigid silicones" as described in U.S. Pat. No. 4,902,499, herein incorporated by reference, having a viscosity above 600,000 cs at 20° C., 700,000 cs plus, and a weight average molecular weight of at least about 500,000, also are useful.

A volatile silicone conditioning agent also is useful in the hair shampoo composition as the water-insoluble hair treating compound, either alone or in conjunction with other water-insoluble hair treating compounds. The volatile silicone normally is a low molecular weight polydimethylsiloxane, however a low molecular weight polydimethylsiloxane including phenyl substituents also is useful. Furthermore, the low molecular weight polydimethylsiloxane compound can be a linear or a cyclic polydimethylsiloxane compound. The volatile polydimethylsiloxane compound provides lubrication and imparts hair conditioning properties to wet hair, and has sufficient volatility to slowly volatilize from the hair such that a residual buildup of silicone compound is not present on dry hair. An example of a linear, low molecular weight, volatile polydimethylsiloxane compound useful in the pearlized shampoo composition is hexamethyldisiloxane, available commercially under the tradename DOW CORNING 200 FLUID, from Dow Corning Corp., Midland, Mich. Hexamethyldisiloxane has a viscosity of 0.65 cs (centistokes), is highly volatile, is nongreasy, provides lubrication, and improves the overall combing properties of the hair. Other linear polydimethylsiloxanes, such as decamethyltetrasiloxane, having a boiling point of about 195° C. and a viscosity of 1.5 centistokes; octamethyltrisiloxane; and decamethylpentasiloxane, also are useful in the composition of the present invention.

In addition, the cyclic, low molecular weight, volatile polydimethylsiloxanes, having the Cosmetic, Toiletry and Fragrance Association designation (CTFA) cyclomethicone, also are useful in the pearlized shampoo composition. The cyclomethicones are low molecular weight, water-insoluble cyclic compounds having an average of about 3 to about 6 —[O—Si(CH$_3$)$_2$]- repeating group units per molecule and boil at atmospheric pressure in a range of from about 150° C. to about 250° C. Suitable cyclomethicones are available commercially under the tradenames SILICONE SF-1173 (octamethylcyclotetrasiloxane) and SILICONE SF-1202 (decamethylcyclopentasiloxane) from General Electric, Waterford, N.Y. and SILICONE 334 FLUID and SILICONE 345 FLUID from Dow Corning Corporation, Midland, Mich., the tetramer being listed first in each instance. The volatile cyclic silicones can be used in combination with a linear volatile silicone, and the volatile silicone conditioner can be used in conjunction with the nonvolatile silicone conditioner.

Another suitable water-insoluble conditioning compound that can be included in a pearlized composition of this embodiment is a nonvolatile hydrocarbon, such as mineral oil. The nonvolatile hydrocarbons provide many of the same benefits as the silicone conditioning agents, and can be included in the composition in conjunction with a silicone conditioning agent.

In addition to nonvolatile hydrocarbon conditioning compounds, a volatile hydrocarbon conditioning compound can be included in the pearlized composition as the water-insoluble hair treating compound, either alone or in conjunction with other water-insoluble hair treating compounds. The volatile hydrocarbon conditioner, such as a hydrocarbon including from about 10 carbon atoms to about 26 carbon atoms, has sufficient volatility to slowly volatilize from the hair to preclude a residual buildup of hydrocarbon on dry hair. The volatile hydrocarbon provides essentially the same benefits as the volatile silicone, such as lubrication and wet hair conditioning.

The preferred volatile hydrocarbon compound is an aliphatic hydrocarbon including from about 12 to about 24 carbon atoms, and has a boiling point in the range of from about 100° C. to about 300° C. Exemplary volatile hydrocarbons are depicted in general structural formula (V), wherein n ranges from 2 to 5.

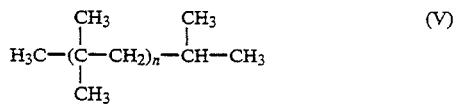

Examples of volatile hydrocarbons useful in the compositions of the present invention are the commercially-available compounds PERMETHYL 99A and PERMETHYL 101A, corresponding to compound of general structure (V) wherein n is 2 and 3, respectively, from Permethyl Corporation, Frazer, Pa. A volatile hydrocarbon compound is useful in the pearlized conditioning composition either alone, in combination with another volatile or nonvolatile hydrocarbon, or in combination with a volatile or nonvolatile silicone.

In another embodiment, the water-insoluble conditioning compound is a fatty alcohol, wherein the fatty alcohol includes from about 12 to about 22 carbon atoms. Exemplary fatty alcohols include, but are not limited to, lauryl alcohol, oleyl alcohol, myristyl alcohol, tallow alcohol, cetyl alcohol, stearyl alcohol, cetearyl alcohol, behenyl alcohol and combinations thereof. A fatty alcohol can be used alone, or in combination with a silicone conditioning agent or a hydrocarbon conditioning agent.

In another embodiment, the water-insoluble conditioning compound is a fatty ester including about 9 to about 34 carbon atoms. The fatty component of the fatty ester can be derived from a fatty acid or a fatty alcohol, or a combination thereof. In addition, the fatty ester can be a straight chain fatty ester, like isopropyl myristate; a branched chain fatty ester, like Purcellin Oil; a benzoate ester, like $C_{12-15}$ alcohols benzoate; or a combination thereof.

For example, a useful class of fatty esters is derived from carboxylic acids having from about six to about 12 carbon atoms, including both branched and straight chain carboxylic acids. In general, the $C_6$ to $C_{12}$ carboxylic acid is esterified with a fatty alcohol including from about 12 to about 22 carbon atoms to provide a fatty ($C_{12}$ to $C_{22}$) ester of a $C_6$ to $C_{22}$ carboxylic acid that is useful in the present invention. Such fatty alcohols include, but are not limited to, lauryl alcohol, myristyl alcohol, cetyl alcohol, cetearyl alcohol, stearyl alcohol, isostearyl alcohol, oleyl alcohol, tallow alcohol, behenyl alcohol and mixtures thereof. Accordingly, fatty ($C_{12}$ to $C_{22}$) esters of $C_6$ to $C_{12}$ carboxylic acids useful in the pearlized shampoo composition of this embodiment include, but are not limited to, cetyl octanoate, stearyl heptanoate, stearyl caprylate, stearyl octanoate, lauryl octanoate, myristyl heptanoate, and oleyl octanoate, or mixtures thereof. These fatty esters can occur naturally or can be synthesized.

In place of, or in combination with, the fatty ($C_{12}$ to $C_{22}$) ester of a $C_6$ to $C_{12}$ carboxylic acid, a fatty ester derived from a fatty acid including from about eight to about 22 carbon atoms esterified with an alcohol including from one to about six carbon atoms can be included in the pearlized shampoo conditioner composition. Examples of such fatty esters include, but are not limited to, isopropyl myristate, isopropyl palmitate, isopropyl laurate, isopropyl linoleate, isopropyl isostearate, isopropyl oleate, isopropyl stearate, isopropyl tallowate, isopropyl ricinoleate, methyl laurate, methyl linoleate, methyl myristate, methyl stearate, methyl ricinoleate, methyl caprylate, methyl oleate, methyl palmitate, methyl stearate, methyl behenate, methyl soyate, methyl tallowate, isopropyl behenate, isopropyl soyate, propyl oleate, butyl oleate, butyl stearate, methyl coconate, methyl lardate, isobutyl palmitate, butyl myristate, ethyl palmitate, ethyl myristate, ethyl oleate, ethyl stearate, isobutyl stearate, isobutyl myristate and combinations thereof.

Another class of fatty esters that can be included in the composition of the present invention, either alone or in combination with the fatty esters described above, is the benzoate esters. Suitable benzoate esters include esters of benzoic acid wherein the esterifying alcohol includes from about eight carbon atoms to about 22 carbon atoms. Examples of suitable benzoate esters include, but are not limited to, the commercial products FINSOLV TN, benzoic acid esterified with fatty alcohols including from about 12 to about 15 carbon atoms; FINSOLV SB, isostearyl benzoate; FINSOLV P, PPG-15 stearyl benzoate; or combinations thereof, all available from Finetex Inc., Elmwood Park, N.J.

Examples of other specific water-insoluble conditioning compounds that can be incorporated into the pearlized conditioning shampoos of this embodiment include, but are not limited to, polysiloxane polyether copolymers, acetylated lanolin alcohols; lanolin-derived extract of sterols and sterol esters; lanolin alcohol concentrate; isopropyl ester of lanolin fatty acids; polyol fatty acid; keratin protein derivatives; aminofunctional silicones; fatty alcohol fraction of lanolin; mineral oil and lanolin alcohol mixture; high molecular weight esters of lanolin; vinylpyrrolidone/ dimethylaminoethylmethacrylate copolymer; 5 mole ethylene oxide adduct of soya sterol; 10 mole ethylene oxide adduct of soya sterol; stearic acid ester of ethoxylated methyl glucoside; hydroxylated lanolin; lactamide MEA; stearamide MEA; mixed ethoxylated and propoxylated long chain alcohols; hydrolyzed animal keratin; ethyl hydrolyzed animal keratin; avocado oil; sweet almond oil; grape seed oil; jojoba oil; apricot kernel oil; sesame oil; hybrid safflower oil; wheat germ oil; ethyl esters of hydrolyzed animal protein; blend of cetyl and stearyl alcohols with ethoxylated cetyl or stearyl alcohols; propoxylated (1-10 moles) lanolin alcohols; isostearamide DEA; and hydrolyzed collagen protein. Other water-insoluble conditioning agents are listed in *CTFA Cosmetic Ingredient Handbook, First Edition*, The Cosmetic Toiletry and Fragrance Association, Inc., New York, N.Y. (1988), pp. 71-73, hereby incorporated by reference.

In accordance with another important embodiment, the shampoo composition including an opacifier of the present invention is an antidandruff shampoo wherein the water-insoluble hair treating compound is an antidandruff agent. The antidandruff agent usually is a particulate compound that is capable of relieving the symptoms of dandruff and is substantive to the hair and scalp to impart residual antidandruff properties between shampoos. Examples of particulate compounds exhibiting antidandruff properties include, but are not limited to, salicylic acid, elemental sulfur, selenium sulfide, zinc pyrithione, a water-insoluble 1-hydroxy pyridone, an azole antimycotic, and undecylenic acid. Particularly advantageous antidandruff agents are zinc pyrithione and elemental sulfur. Zinc pyrithione is the zinc complex of 2-pyridinethiol-1-oxide, and is available commercially from Olin Corp. under the brand name of ZINC OMADINE. Useful sulfurs include elemental sulfur of sufficient purity and particle size to function as an antidandruff agent, as is well known to those skilled in the art.

The antidandruff agents generally are extremely water insoluble and, therefore, are present in the antidandruff shampoo composition as discrete solid particles. These particles should be homogeneously dispersed and suspended throughout the shampoo to ensure that the consumer receives an efficacious dose of the antidandruff agent at each shampooing. Without a suspending agent, the antidandruff agent can completely separate from the antidandruff shampoo composition resulting in poor dandruff control, and ultimately in consumer dissatisfaction and complaints. Therefore, a suspending agent is incorporated into the basic antidandruff formulation to retard, minimize or eliminate settling of the insoluble antidandruff agent. In general, an opacifier of the present invention effectively helps suspend a particulate antidandruff agent, and other particulate hair treating compounds.

In addition to the above-described ingredients, other common cosmetic components and additives can be included in a shampoo composition including an opacifier of the present invention, as long as the basic properties of the shampoo composition and opacifier are not adversely affected. Such optional cosmetic components and additives include, but are not limited to, fragrances, dyes, hair colorants, thickeners, hair conditioners, hydrotropes, foam stabilizers, inorganic salts, humectants, solubilizers, preservatives, water softening agents, buffers and the like. These optional components and additives usually are present in weight percentages of 0% up to about 5% by weight of the shampoo composition each, and usually 0% to about 20% by weight of the shampoo composition in total.

The composition also can include optional conditioning agents and emulsifiers. In general, such optional conditioning agents and emulsifiers, like quaternary ammonium compounds, are well-known to those skilled in the art, and can be included in the present shampoo composition in an amount of 0% to about 5% by weight of the composition.

In any composition pearlized by an opacifier of the present invention, the carrier of the composition is predominantly water, but nonaqueous solvents also can be included to help solubilize composition ingredients that are not sufficiently soluble in water, to adjust the viscosity of the composition, or to act as a humectant. Suitable solvents include polyols, like glycerol; glycols, like ethylene glycol, propylene glycol and hexylene glycol; or mixtures thereof. The optional nonaqueous solvents should not adversely affect the pearlized composition with respect either to composition stability or to composition performance, or adversely affect the consumer appeal of the composition. A nonaqueous solvent can be present in a water-based composition including an opacifier of the present invention in an amount of 0% up to about 5% by weight of the composition.

The opacifier of the present invention is used to opacify or pearlize relatively thin through relatively thick water-based compositions. To achieve the full advantage of the present invention, the opacifier is included in a moderately viscous composition, e.g., a composition having a viscosity in the range of from about 1000 cps (centipoises) to about 15,000 cps. In addition, the opacifier can be included in an emulsified composition or in a true solution to impart a pearlescent or opacified effect. If the composition is emulsified, generally the emulsion is stable and resists phase separation or settling of composition ingredients at a temperature of about 20° C. to about 25° C. essentially indefinitely. The emulsifying properties of the present opacifier assist in stabilizing the emulsion. Compositions including the present opacifier have demonstrated sufficient resistance to phase separation, and to settling of particulate ingredients, at temperatures normally found in commercial product storage and shipping to remain unaffected for periods of one year or more because of the suspending properties demonstrated by the opacifier.

In accordance with the present invention, several hair care compositions were prepared to demonstrate the opacifying properties of the present opacifier, the improved suspending properties provided by the present opacifier, and the ability of the hair care composition to cleanse the hair and to deliver a water-insoluble hair treating compound to the hair or scalp provided by a water-based hair care composition comprising a cleansing surfactant and/or a water-insoluble hair treating compound; and an opacifying agent comprising an amine compound of general structural formula (I) or (II) or (III) and a suitable acid. It has been demonstrated that to maximize suspension properties of the opacifier, the hair care composition should include the amine and the acid in sufficient amounts such that essentially no solid particles of the amine are present in the composition.

It should be noted however that the acid of the opacifier is not necessarily present in an equimolar, or equimolar equivalent, amount in relation to the amine present in the opacifier. A stoichiometric amount of acid in relation to the amine is not necessarily required because other ingredients in the hair care composition may neutralize a portion of the amine. Therefore, a stoichiometric amount of acid can be included in the composition. However, as little as 20% of the stoichiometric amount of acid can be added to sufficiently neutralize the amine depending upon the particular composition ingredients and the desired pH of the composition. An excess amount of acid does not adversely affect the ability of the opacifier to pearlize the composition and suspend composition ingredients, but also does not increase opacifier performance, and therefore is wasted except for the purposes of adjusting a composition property, such as pH.

Although the mechanism of interaction between the amine, the acid and other composition ingredients that imparts a pearlescent effect and suspends water-insoluble compounds is not known precisely, it has been theorized that the acid-neutralized amine forms a network that suspends the water-insoluble compound. Incomplete water solubility helps provide the pearlescent effect. It should be noted that a hair care composition including only free amine, i.e., an amine compound of general structural formula (I) or (II) or (III) that is not neutralized with an acid, does not provide a pearlescent effect and the composition undergoes a phase separation relatively rapidly, such as in less than 24 hours. Accordingly, it is the acid-neutralized amine compound that opacifies the composition and helps suspend the water-insoluble compound in the water-based composition. Furthermore, laboratory and salon tests have shown that hair shampooed with a hair care composition including an opacifier of the present invention is effectively cleansed and that the water-insoluble hair treating compound is effectively delivered to the hair or scalp. Accordingly, the present opacifier does not adversely affect performance of the hair care composition.

To demonstrate the new and unexpected results achieved by the method and composition of the present invention, the following Examples 1 through 20 were prepared by an identical method. Each composition of Examples 1 through 20 is a conditioning shampoo including an anionic surfactant, a water-insoluble silicone conditioning agent and an opacifier of the present invention. The compositions were prepared by a method wherein the anionic cleansing surfactant, as an approximately 30% by weight aqueous solution, first was added to a vessel, then heated to about 180° F. under moderate agitation. Then the amine compound of general structural formula (I) or (II) or (III) was added to the vessel, followed by the acid. The resulting mixture was maintained at about 180° F., and stirred from about 30 minutes to about 90 minutes to homogenize the mixture and form an aqueous emulsion of the amine salt opacifier. The remaining amount of water was added to cool the mixture, then the remaining ingredients were added to the resulting mixture individually, and in any desired order. Agitation speed was increased after addition of the water-insoluble hair treating compound to effectively disperse the water-insoluble hair treating compound and the opacifier throughout the composition.

| Ingredient | EX. 1[1)] | EX. 2 | EX. 3 | EX. 4 | EX. 5 | EX. 6 | EX. 7 |
|---|---|---|---|---|---|---|---|
| Ammonium Lauryl Sulfate[2)] | 6.0 | 6.0 | 6.0 | 6.0 | 6.0 | 6.0 | 6.0 |
| Sodium Lauryl Sulfate[3)] | 4.5 | 4.5 | 4.5 | 4.5 | 4.5 | 4.5 | 4.5 |
| Ammonium Lauryl Ether Sulfate | 2.8 | 2.8 | 2.8 | 2.8 | 2.8 | 2.8 | 2.8 |
| Lauramide DEA | 1.25 | 1.25 | 1.25 | 1.25 | 1.25 | 1.25 | 1.25 |
| ADOGEN 232[4)] | 3.0 | 3.0 | 3.0 | 3.0 | 3.0 | — | — |
| ADOGEN 140[5)] | — | — | — | — | — | 3.0 | 3.0 |
| ADOGEN 240[6)] | — | — | — | — | — | — | — |
| ADOGEN 540D[7)] | — | — | — | — | — | — | — |
| Citric Acid[8)] | 0.55 | 0.55 | 0.55 | 0.55 | — | — | — |
| Lactic Acid[9)] | — | — | — | — | 0.79 | 0.79 | 0.79 |
| Sulfuric Acid[10)] | — | — | — | — | — | — | — |
| Phosphoric Acid[11)] | — | — | — | — | — | — | — |
| Hydrochloric Acid[12)] | — | — | — | — | — | — | — |
| Silicone Blend[13)] | 2.00 | 2.00 | 2.00 | 2.00 | 2.00 | 2.00 | 2.00 |
| Tetrasodium EDTA[14)] | 0.08 | 0.08 | 0.08 | 0.08 | 0.08 | 0.08 | 0.08 |
| Dye | 0.11 | 0.11 | 0.11 | 0.11 | 0.11 | 0.11 | 0.11 |
| Fragrance | 0.50 | 0.50 | 0.50 | 0.50 | 0.50 | 0.50 | 0.50 |
| Preservative[15)] | 0.13 | 0.13 | 0.13 | 0.13 | 0.13 | 0.13 | 0.13 |
| Ammonium Xylene Sulfonate | 0.18 | 0.18 | 0.18 | 0.18 | 0.18 | 0.18 | 0.18 |
| Soft Water | q.s. | q.s. | q.s. | q.s. | q.s. | q.s. | q.s. |
| Appearance: | Pearlescent | Pearlescent | Pearlescent | Pearlescent | Pearlescent | Pearlescent | Pearlescent |
| pH: | 5.3 | 5.4 | 5.3 | 5.7 | 5.5 | 7.4 | 5.8[17)] |
| Viscosity (in Cps)[16)]: | 3230 | 3010 | 2650 | 3700 | 1780 | 4320 | 1880 |
| Ingredient | EX. 8[1)] | EX. 9 | EX. 10 | EX. 11 | EX. 12 | EX. 13 | EX. 14 |
| Ammonium Lauryl Sulfate[2)] | 6.0 | 6.0 | 6.0 | 6.0 | 6.0 | 6.0 | 6.0 |
| Sodium Lauryl Sulfate[3)] | 4.5 | 4.5 | 4.5 | 4.5 | 4.5 | 4.5 | 4.5 |
| Ammonium Lauryl Ether Sulfate | 2.8 | 2.8 | 2.8 | 2.8 | 2.8 | 2.8 | 2.8 |
| Lauramide DEA | 1.25 | 1.25 | 1.25 | 1.25 | 1.25 | 1.25 | 1.25 |
| ADOGEN 232[4)] | — | 3.0 | 3.0 | — | — | — | — |
| ADOGEN 140[5)] | 3.0 | — | — | — | — | — | — |
| ADOGEN 240[6)] | — | — | — | 3.0 | 3.0 | 3.0 | 3.0 |
| ADOGEN 540D[7)] | — | — | — | — | — | — | — |
| Citric Acid[8)] | — | — | — | — | 0.55 | — | — |
| Lactic Acid[9)] | 0.66 | 0.71 | 0.70 | 0.62 | — | — | — |
| Sulfuric Acid[10)] | — | — | — | — | — | 0.15 | — |

-continued

| Ingredient | | | | | | | |
|---|---|---|---|---|---|---|---|
| Phosphoric Acid[11] | — | — | — | — | — | — | 0.26 |
| Hydrochloric Acid[12] | — | — | — | — | — | — | — |
| Silicone Blend[13] | 2.00 | 2.00 | 2.00 | 2.00 | 2.00 | 2.00 | 2.00 |
| Tetrasodium EDTA[14] | 0.08 | 0.08 | 0.08 | 0.08 | 0.08 | 0.08 | 0.08 |
| Dye | 0.11 | 0.11 | 0.11 | 0.11 | 0.11 | 0.11 | 0.11 |
| Fragrance | 0.50 | 0.50 | 0.50 | 0.50 | 0.50 | 0.50 | 0.50 |
| Preservative[15] | 0.13 | 0.13 | 0.13 | 0.13 | 0.13 | 0.13 | 0.13 |
| Ammonium Xylene Sulfonate | 0.18 | 0.18 | 0.18 | 0.18 | 0.18 | 0.18 | 0.18 |
| Soft Water | q.s. | q.s. | q.s. | q.s. | q.s. | q.s. | q.s. |
| Appearance: | Pearlescent | Pearlescent | Pearlescent | Pearlescent | Pearlescent | Pearlescent | Pearlescent |
| pH: | 6.0[18] | 6.0 | 6.1 | 5.6 | 5.9 | 8.1 | 7.0 |
| Viscosity (in Cps)[16]: | 4220 | 2300 | 2250 | 11,500 | 7100 | 10,600 | 7580 |

| Ingredient | EX. 15[1] | EX. 16 | EX. 17 | EX. 18 | EX. 19 | EX. 20 |
|---|---|---|---|---|---|---|
| Ammonium Lauryl Sulfate[2] | 6.0 | 6.0 | 6.0 | 6.0 | 6.0 | 9.3 |
| Sodium Lauryl Sulfate[3] | 4.5 | 4.5 | 4.5 | 4.5 | 4.5 | 5.0 |
| Ammonium Lauryl Sulfate | 2.8 | 2.8 | 2.8 | 2.8 | 2.8 | 1.6 |
| Lauramide DEA | 1.25 | 1.25 | 1.25 | 1.25 | 1.25 | 0.7 |
| ADOGEN 232[4] | — | — | — | — | — | — |
| ADOGEN 140[5] | — | — | — | — | — | — |
| ADOGEN 240[6] | 3.0 | 3.0 | 3.0 | 3.0 | 3.0 | — |
| ADOGEN 540D[7] | — | — | — | — | — | 5.0 |
| Citric Acid[8] | — | — | — | — | — | 2.0 |
| Lactic Acid[9] | — | — | — | — | — | — |
| Sulfuric Acid[10] | — | 0.30 | — | — | — | — |
| Phosphoric Acid[11] | 0.51 | — | — | — | — | — |
| Hydrochloric Acid[12] | — | — | 0.22 | 0.20 | 0.20 | — |
| Silicone Blend[13] | 2.00 | 2.00 | 2.00 | 2.00 | 2.00 | 2.00 |
| Tetrasodium EDTA[14] | 0.08 | 0.08 | 0.08 | 0.08 | 0.08 | 0.08 |
| Dye | 0.11 | 0.11 | 0.11 | 0.11 | 0.11 | q.s. |
| Fragrance | 0.50 | 0.50 | 0.50 | 0.50 | 0.50 | — |
| Preservative[15] | 0.13 | 0.13 | 0.13 | 0.13 | 0.13 | 0.15 |
| Ammonium Xylene Sulfonate | 0.18 | 0.18 | 0.18 | 0.18 | 0.18 | 0.10 |
| Soft Water | q.s. | q.s. | q.s. | q.s. | q.s. | q.s. |
| Appearance: | Pearlescent | Pearlescent | Pearlescent | Pearlescent | Pearlescent | Pearlescent |
| pH: | 5.7 | 6.2 | 5.5 | 6.3 | 6.3 | 5.9 |
| Viscosity (in Cps)[16]: | 9980 | 8820 | 10,260 | 4500 | 4100 | — |

[1] Percent by weight of active ingredient in the composition;
[2] Added as a 30% by weight active solution;
[3] Added as a 30% by weight active solution;
[4] A secondary amine based on 85–90% by weight straight chain alcohols and 10–15% by weight branched alcohols including from about 16 to about 22 carbon atoms, available from Sherex Chemical Co., Inc., Dublin, Ohio;
[5] Hydrogenated tallow amine, a primary amine, a primary amine available from Sherex Chemical Co., Dublin, Ohio;
[6] Di(hydrogenated tallow)amine, a secondary amine available from Sherex Chemical Co., Dublin, Ohio;
[7] Hydrogenated tallow diamine, a diamine available from Sherex Chemical Co., Dublin, Ohio;
[8] Added as a 50% by weight aqueous solution;
[9] Added as an 88% by weight aqueous solution;
[10] Added as a 50% by weight aqueous solution;
[11] Added as an 85–88% by weight aqueous solution;
[12] Added as a 36% by weight aqueous solution;
[13] Added as a 100% active blend including one part by weight Silicone GUM SE-30, a polydimethylsiloxane having a viscosity of about 15 × 10$^6$ to about 30 × 10$^6$; and two parts by weight of Silicone Fluid 96-350, a polydimethylsiloxane having a viscosity of about 350 centipoises, both available from General Electric Silicone Products Division, Waterford, NY;
[14] Added as a 39% aqueous solution of tetrasodium ethylenediaminetetraacetate;
[15] DMDM hydantoin and methylchloroisothiazolinone;
[16] Viscosity in centipoises;
[17] pH after preparation of the composition was 4.37, then the pH was adjusted to 5.8 with sodium hydroxide; and
[18] pH after preparation of the composition was 7.7, then the pH was adjusted to 6.0 with lactic acid.

The compositions of Examples 1 through 4 were identical except the composition of Examples 1 and 4 were emulsified at about 180° F. for 30 minutes, whereas the composition of Example 2 was emulsified for 60 minutes and the composition of Example 3 was emulsified for 90 minutes. The shampoo-conditioner compositions of Examples 1–4 were essentially identical, with each composition exhibiting excellent pearlescence and maintaining phase stability at 110° F. and 120° F. after 24 hours. The composition of Example 5 was similar to the compositions of Examples 1 through 4 except lactic acid was substituted for citric acid. The composition of Example 5 demonstrated properties essentially identical to the compositions of Examples 1–4. Accordingly, pearlescent shampoo-conditioner compositions resulted from emulsions of the opacifier that were emulsified for at least 30 minutes, and substitution of an organic aliphatic carboxylic acid for an inorganic mineral acid did not adversely affect either the ability of the opacifier to pearlize the composition or composition stability. The compositions of Examples 9 and 10 were essentially identical repeats of the compositions of Example 5, except the compositions of Examples 9 and 10 were cooled quickly. The compositions of Examples 9 and 10 exhibited an excellent pearlescent effect and were phase stable one week after preparation.

The compositions of Examples 6 through 8 utilized a primary amine and lactic acid. The compositions were pearlescent and stable, exhibiting essentially no phase separation after storage at 110° F. or at 120° F. for 6 months. Accordingly, either a primary amine (Examples 6–8) or a secondary amine (Examples 1–4) can be included as the amine component of the opacifier of the present invention.

The compositions of Examples 11 through 19 utilized a different secondary amine (ADOGEN 240) and varied the acid component of the opacifier. Each composition of Examples 11–19 was effectively pearlized and each composition effectively resisted phase separation at 110° F. and 120° F. for a period of at least 6 months, and further demonstrated that the acid component of the opacifier can be an organic carboxylic acid or an inorganic mineral acid. The composition of Example 20 utilized a diamine of general structural formula (III) (ADOGEN 540D). The composition of Example 20 was effectively opacified and resisted phase separation after two months storage at room temperature, at 110° F., and at 120° F.

To further demonstrate the ability of an amine having the general structural formula (I) or (II) or (III) and a suitable acid to opacify, or pearlize, a water-based composition, different combinations of various amines and various acids were tested for an ability to opacify, and to suspend, a silicone blend, or a combination of a silicone blend and sulfur, in a water-based composition. In each test, the water-based composition included 2% by weight of a silicone blend including one part by weight Silicone GUM SE-30 and 2 parts by weight SF 96-350 Silicone Fluid. The composition did not include a cleansing surfactant. Accordingly, the compositions would be useful as hair conditioning compositions.

Therefore, from the compositions of Examples 21 through 40 listed in TABLE I, it was shown that the combination of an amine of general structural formula (I) or (II) or (III) and a suitable acid opacifies the water-based composition, and helps suspend the silicone and, when present, the sulfur. In the compositions of Examples 21 through 40, summarized in TABLE I, the amine was present in an amount of from about 3% to about 5% by weight; the acid was present in an amount of from about 0.5% to about 1.6% by weight.

TABLE I

| Opacifiers Including an Amine and an Acid | | |
|---|---|---|
| Example | Amine | Acid |
| 21 | Hydrogenated Tallow Amine[1] (3%)[2] | Phthalic Acid (0.95%)[3] |
| 22 | Hydrogenated Tallow Amine (3%) | Salicylic Acid (1.58%) |
| 23 | ADOGEN 232[5] (3%) | Phthalic Acid (0.50%) |
| 24 | ADOGEN 232 (3%) | Citric Acid (0.50%) |
| 25 | ADOGEN 232 (3%) | Phosphoric Acid (0.80%) |
| 26 | Di(Hydrogenated Tallow) Amine[6] (3%) | Phthalic Acid (0.50%) |
| 27 | Di(Hydrogenated Tallow) Amine (3%) | Salicylic Acid (0.86%) |
| 28 | Di(Hydrogenated Tallow) Amine (3%) | Citric Acid (0.45%) |
| 29 | Di(Hydrogenated Tallow) Amine (3%) | Benzoic Acid (1.00%) |
| 30 | Distearyl Amine[7] (3%) | Phthalic Acid (0.50%) |
| 31 | Distearyl Amine (3%) | Salicylic Acid (0.84%) |
| 32 | Distearyl Amine (3%) | Benzoic Acid (1.00%) |
| 33 | Tri(Hydrogenated Tallow) Amine[8] (3%) | Phthalic Acid (0.34%) |
| 34 | Tri(Hydrogenated Tallow) Amine (3%) | Salicylic Acid (0.58%) |
| 35 | Di(Hydrogenated Tallow) Methyl Amine[9] (3%) | Phthalic Acid (0.49%) |
| 36 | Di(Hydrogenated Tallow) Methyl Amine (3%) | Salicylic Acid (0.84%) |
| 37 | Distearyl Methyl Amine[10] (3%) | Phthalic Acid (0.48%) |
| 38 | Distearyl Methyl Amine (3%) | Salicylic Acid (0.82%) |
| 39 | Stearamidopropyl Dimethylamine[11] (3%) | Citric Acid (0.53%) |
| 40 | Stearamidoethyl Diethylamine[12] (5%) | Citric Acid (0.55%) |

[1]ADOGEN 140, a primary amine, available, as are all other ADOGEN amines, from Sherex Chemical Co., Dublin, Ohio;
[2]percent by weight of amine in the composition;
[3]percent by weight of acid in the composition;
[4]composition includes 2% silicone blend and 6.37% sulfur-Carbopol slurry (2.03% elemental sulfur);
[5]secondary amine including 85–90% by weight straight chain alcohols and 10–15% by weight branched alcohols including from about 16 to about 22 carbon atoms;
[6]ADOGEN 240, a secondary amine;
[7]ADOGEN 249, a secondary amine;
[8]ADOGEN 340, a tertiary amine;
[9]ADOGEN 343, a tertiary amine;
[10]ADOGEN 349, a tertiary amine;
[11]LEXAMINE S-13, an amine of general structural formula (II), available from Inolex Chemical Div., Philadelphia, PA.; and
[12]LEXAMINE 22, an amine of general structural formula (II), available from Inolex Chemical Div., Philadelphia, PA.

Each hair conditioning composition of Examples 21–40 was a pearlescent composition that effectively suspended the silicone and the sulfur after storage at room temperature and at 120° F. for 3 months. In some of the compositions, such as 21, 22, 30, 31, 32 and 39, a slight phase separation was observed. However, the separated phase did not include silicone. Therefore, the silicone was effectively suspended by the opacifier of the present invention. In compositions including a tertiary amine, it was found that flocculation, or curdling, of the composition can occur after one day of storage at 120° F. (composition of Examples 33 and 34), however the silicone remains suspended in the composition. The best pearlescent effect was demonstrated in Example 21 and 22, thereby showing that a primary amine provides the full advantage of the present invention.

Overall, the compositions of Examples 21 through 40 of TABLE I show that a primary, secondary or tertiary amine having the general structural formula (I) or (III) or an amine having the general structural formula (II), when neutralized with a sufficient amount of a suitable acid, effectively opacifies a water-based composition, and effectively helps suspend a water-insoluble compound, either liquid or particulate, in a water-based composition. Further, TABLE I, and Examples 1-20, show that an inorganic mineral acid (e.g., composition of Example 25), an aliphatic carboxylic acid (e.g., composition of Examples 24 and 28) or an aromatic carboxylic acid (e.g., composition of Examples 21-23, 26-27, and 29-40) is a suitable acid to neutralize the amine of and 0.90% of the alkanolamide lauramide DEA. TABLE II lists the particular amine and particular acid used in each composition of Examples 41 through 60, the amount of amine and acid included in each composition, and the appearance and stability of each water-based composition. The percentages included in TABLE II are the weight percentages of the active amount of amine and acid included in each composition.

TABLE II

Stability of Shampoo Compositions Including an Amine-Acid Opacifier

| Example | Amine | Acid | Stability | Appearance |
|---|---|---|---|---|
| 41 | ADOGEN 140 (3%) | LACTIC (.84%) | Stable at room temperature, unstable at 120° F., silicone suspended at both temp. | Excellent pearlescence |
| 42 | ADOGEN 140 (34%) | LACTIC (.88%) | Stable at room temperature, unstable at 120° F., silicone suspended at both temp. | Excellent pearlescence |
| 43 | ADOGEN 140 (2.51%) | LACTIC (.70%) | Stable at room temperature, unstable at 120° F., silicone suspended at both temp. | Excellent pearlescence |
| 44 | ADOGEN 140 (2.0%) | LACTIC (.56%) | Stable at room temperature, unstable at 120° F., silicone suspended at both temp. | Excellent pearlescence |
| 45 | ADOGEN 232 (3%) | CITRIC (.55%) | Stable at all temp., mucilaginous at 120° F. | Poor pearlescence |
| 46 | ADOGEN 232 (2.5%) | CITRIC (.45%) | Stable at all temp., mucilaginous at 120° F. | Poor pearlescence |
| 47 | ADOGEN 232 (2.0%) | CITRIC (.35%) | Stable at all temp., mucilaginous at 120° F. | Poor pearlescence |
| 48 | ADOGEN 232 (1.5%) | CITRIC (.25%) | Stable at all temp., mucilaginous at 120° F. | Poor pearlescence |
| 49 | ADOGEN 232 (3%) | LACTIC (.79%) | Stable at all temp., mucilaginous at 120° F. | Poor pearlescence |
| 50 | ADOGEN 232 (2.5%) | LACTIC (.66%) | Stable at all temp., mucilaginous at 120° F. | Poor pearlescence |
| 51 | ADOGEN 232 (2.0%) | LACTIC (.53%) | Stable at all temp., mucilaginous at 120° F. | Poor pearlescence |
| 52 | ADOGEN 232 (1.5%) | LACTIC (.40%) | Stable at all temp., mucilaginous at 120° F. | Poor pearlescence |
| 53 | ADOGEN 232 (3%) | CITRIC (1.58%) | Stable at all temp., mucilaginous at 120° F. | Poor pearlescence pH too low |
| 54 | ADOGEN 240 (3%) | LACTIC (.62%) | Stable at all temp. | Good pearlescence |
| 55 | ADOGEN 240 (3%) | PHOSPHORIC (.51%) | Stable at all temp. pearlescence | Good |
| 56 | ADOGEN 240 (3%) | SULFURIC (.30%) | Stable at all temp. pearlescence | Good |
| 57 | ADOGEN 240 (3%) | HYDROCHLORIC (.22%) | Stable at all temp. pearlescence | Good |
| 58 | ADOGEN 240 (2.5%) | HYDROCHLORIC (.18%) | Stable at all temp. pearlescence | Good |
| 59 | ADOGEN 240 (2.0%) | HYDROCHLORIC (.14%) | Stable at all temp. pearlescence | Good |
| 60[1)] | ADOGEN 240 (3.0%) | HYDROCHLORIC (.22%) | Stable at all temp. pearlescence | Poor |

[1)]Composition includes 12.10% by weight ammonium lauryl sulfate as the sole anionic surfactant.

the present opacifier. TABLE I also shows that an amine of general structural formula (I) (Examples 21-38) or that an amine of general structural formula (II) (Examples 39 and 40), after neutralization by a sufficient amount of a suitable acid, effectively opacifies a water-based composition and effectively helps suspend a water-insoluble compound in a water-based composition.

To further demonstrate the opacifying capabilities of an opacifier of the present invention, various amines and acids, in varying amounts, were used as the opacifier in a water-based composition that included 2% by weight of a water-insoluble silicone blend of 1 part Silicone GUM SE-30 and 2 parts by weight SF 96-350 Silicone Fluid; 12.10% by weight, in total, of the cleansing surfactants ammonium lauryl sulfate, ammonium lauryl ether sulfate (1 mole EO) and/or sodium lauryl sulfate;

TABLE II shows that a variety of amines having general structural formula (I) can be neutralized with a variety of inorganic acids or organic carboxylic acids to provide an effective opacifier for a shampoo composition including a water-insoluble compound. In TABLE II, pearlescence was determined subjectively, with the term "good pearlescence" meaning the pearlescence exhibited by SUAVE, a leading opacified hair shampoo conditioner available commercially from Helene Curtis, Inc., Chicago, Ill. The term "excellent pearlescence" means an esthetically improved pearlescence over SUAVE; the term "poor pearlescence" means an inferior pearlescence compared to that exhibited by SUAVE. In general, TABLE II shows that to achieve the full advantage of the present invention, the amine of general structural formula (I) used in the opacifier is a primary amine (Examples 41 through 44). TABLE II also shows that the present opacifier helps suspend the water-insoluble silicone in the composition. In addition, compositions of Examples 54 through 60 were subjected to laboratory and beauty center evaluations, and found to have physical and esthetic properties, such as wet and dry combing, cleansing performance, lather and feel, that equal the properties exhibited by SUAVE.

To demonstrate the effect of varying the amount of acid in the composition, the secondary amine di(hydrogenated tallow)amine (ADOGEN 240), at 3% by weight, was included in a composition further including 12.10% by weight in total of anionic cleansing surfactants. Varying amounts of citric acid were included to determine the effects of an increased amount of acid in the composition on the ability of the ADOGEN 240 and citric acid to opacify the composition, to suspend a water-insoluble compound and to provide an esthetically pleasing, and therefor consumer acceptable, water-based shampoo composition. TABLE III summarizes the compositions of Examples 61 through 71, showing the amount of citric acid included in the water-based composition (Examples 61–66), and the different water-insoluble compounds included in the composition (Examples 63, 67 and 68). TABLE III also illustrates water-based compositions including a fatty acid having more than 12 carbon atoms as the acid of the opacifier (Examples 69–71).

TABLE III

Effect of an Increased Amount of Acid in the Opacifier and Effect of Using a Fatty Acid in the Opacifier

| EX. | Amount of Acid | pH | Water-Insoluble Hair-Treating Compound |
|---|---|---|---|
| 61[1] | Citric (0.25%) | 9.58 | Silicone Blend (2%)[2] |
| 62[3] | Citric (0.33%) | 7.16 | Silicone Blend (2%) |
| 63 | Citric (0.48%) | 5.71 | Silicone Blend (2%) |
| 64 | Citric (0.96%) | 4.54 | Silicone Blend (2%) |
| 65 | Citric (1.44%) | 3.97 | Silicone Blend (2%) |
| 66 | Citric (1.92%) | 3.65 | Silicone Blend (2%) |
| 67 | Citric (0.45%) | 6.09 | Sulfur (elemental 2.03%, included in Carbopol-sulfur dispersion) |
| 68 | Citric (0.45%) | 5.81 | Zinc Pyrithione (2.1%) |
| 69 | Oleic (6.0%) | 5.97 | Silicone Blend (2%) |
| 70[4] | Oleic (3.5%) | 6.10 | Silicone Blend (2%) |
| 71[4] | Stearic (3.5%) | 5.80 | Silicone Blend (2%) |

[1] All compositions of Examples 61 through 71 included a total of 12.10% by weight anionic surfactant; and the compositions of Examples 61 through 69 included 3% by weight ADOGEN 240;
[2] Silicone blend including 33% 1 part by weight Silicone GUM SE-30 and 2 parts by weight SF 96-350 Silicone Fluid;
[3] Added 1% sodium chloride to increase viscosity; and
[4] Composition included 1% by weight ADOGEN 240.

The compositions of Examples 61 and 62 were opacified water-thin liquids. Sodium chloride was added to the composition of Example 62 to increase the viscosity to 4850 cps. The compositions of Examples 61 and 62 also were stable at room temperature, and at 120° F., for four weeks, exhibiting no phase separation. Therefore, it has been demonstrated that the present compositions are sufficiently opacified and help suspend the water-insoluble hair treating compound by a mechanism other than thickening. The compositions of Examples 63–66 also were opacified and stable at room temperature and at 120° F., showing no silicone separation after 4 weeks of storage. The compositions of Examples 67 and 68, each including a particulate antidandruff agent, demonstrated an excellent pearlescence and an ability to suspend the particulate antidandruff agent with no separation or settling observed at room temperature, or at 120° F., after two weeks of storage.

The compositions of Examples 69 through 71 each utilized an aliphatic carboxylic acid including more than 12 carbon atoms, i.e. a fatty acid, to neutralize the secondary amine. Each composition was stable, exhibiting no silicone phase separation after 24 hours. The composition of Example 69 was a very thick, cream-like composition, whereas the compositions of Examples 70 and 71, each including only 1% by weight of the secondary amine were pearlized compositions of low viscosity. Accordingly, a fatty acid including more than twelve carbon atoms is useful in neutralizing an amine of general structural formula (I) or (II) or (III), which in turn effectively opacifies the composition and helps suspend a water-insoluble compound in a water-based shampoo composition.

A fatty acid including more than 12 carbon atoms provides a composition that generally is too thick for consumer acceptance at the higher levels of amine, e.g., about 3%, included in the composition. However, compositions having a consumer acceptable viscosity are provided when a fatty acid including more than 12 carbon atoms and about 1% of an amine is included in the composition. A fatty acid including olefinic unsaturation, e.g., the oleic acid used in Examples 69 and 70, effectively neutralized the amine and helped suspend the water-insoluble hair treating compound, but provided a composition of decreased consumer acceptability because the resulting shampoo was too thick and demonstrate decreased composition esthetics. Therefore, in summary, to achieve the full advantage of the present invention in regard to consumer esthetics, the aliphatic carboxylic acid utilized to neutralize the amine is a saturated acid; includes about 12 or fewer carbon atoms; and is used in a sufficient amount such that no solid particles of an amine of general structural formula (I) or (II) or (III) is present in the opacified hair shampoo.

The opacifier of the present invention also effectively opacifies water-based compositions that do not include a water-insoluble compound. Examples 72 through 106, in TABLE IV, show that a water-based shampoo, including an anionic surfactant, is opacified by an amine of general structural formula (I) and a sufficient amount of a suitable acid. The appearance of the opacified composition can be varied to provide a desired opacified effect by a judicious selection of both a particular amine and a particular acid, and the amount of each component.

TABLE IV

| | | SHAMPOOS OPACIFIED WITH AN AMINE AND ACID | | | | | |
|---|---|---|---|---|---|---|---|
| Ex-ample | | Amine (%)[1] | Acid (%)[1] | Initial Appearance[2] | 24 hrs.[3] | | Storage[4] | |
| | | | | | RT | 120° F. | RT | 120° F. |
| 72[5] | A | ADOGEN 140 3 | CITRIC 1.1 | WV,O,F[7] | MP,HV,O | SV,H,C | VELP,MV,O | SV,H,C |
| | B | ADOGEN 140 3 | CITRIC 1.2 | SP,O,SV | WV,O,SP | WV,H,C | N/A[8] (5 days) | SV,H,C (5 days) |
| 73 | A | ADOGEN 140 3 | PHOS. .9 | WV,0,FP | WV,O,SP | WV,H,C | VELP,MV,O | SV,H,C |
| | B | ADOGEN 140 3 | PHOS. 1.0 | O,SV,SP | SV,O,SP | WV,H,C | N/A | N/A |
| | A (S) | ADOGEN 140 3 | PHOS. 1.0 | O,VELP,MV | O,VELP,HV | N/A | N/A | N/A |

TABLE IV-continued
SHAMPOOS OPACIFIED WITH AN AMINE AND ACID

| Example | | Amine (%)[1] | Acid (%)[1] | Initial Appearance[2] | 24 hrs.[3] RT | 120° F. | Storage[4] RT | 120° F. |
|---|---|---|---|---|---|---|---|---|
| 74 | A | ADOGEN 140 1 | CITRIC .4 | WV,C | H,O | WV,C | (5 days) O,VELP,SV | (5 days) N/A |
| | B | ADOGEN 140 1 | CITRIC .6 | WV,H | H,Pr | WV,H,C,Pr | O,VELP,SV | N/A |
| 75 | A | ADOGEN 140 1 | PHOS. .3 | WV,C,FP | H,O,C | WV,C | (4 days) HV,O,VELP | N/A |
| | B | ADOGEN 140 1 | PHOS. .4 | SV,H,FP | H,Pr | WV,H,C | MV,O,VELP | N/A |
| 76 | A | ADOGEN 240 3 | CITRIC 1@[9] | WV,O,SP | VV,O,SP | WV,O,SP | N/A | N/A |
| | B | ADOGEN 240 3 | CITRIC 1@ | WV,O,MP | WV,O,MP | WV,O,MP | N/A | N/A |
| 77 | A | ADOGEN 240 3 | PHOS. .7@ | WV,O,SP | WV,O,SP | WV,C,O,MP | N/A | N/A |
| | B | ADOGEN 240 3 | PHOS. .7@ | WV,O,MP | WV,O,MP | WV,O,MP | N/A | N/A |
| | A(S) | ADOGEN 240 3 | PHOS. .76 | MV,GP,O | VGP,O,MV | N/A | N/A | N/A |
| | B(S) | ADOGEN 240 3 | PHOS. .7@ | EP,HV,O | EP,HV,O | N/A | N/A | N/A |
| 78 | A | ADOGEN 240 1 | CITRIC .33@ | WV,VH,FP | WV,O,FP | C,O,SP,FL,WV | N/A | N/A |
| | B | ADOGEN 240 1 | CITRIC .33@ | WV,O,SP | WV,O,SP | C,O,SP,FL,WV | N/A | N/A |
| | A (S) | ADOGEN 240 1 | CITRIC .33@ | SV,O,VGP | SV,O,VGP | N/A | N/A | N/A |
| | B (S) | ADOGEN 240 1 | CITRIC .33@ | HV,O,EP | HV,O,EP | N/A | N/A | N/A |
| 79 | A | ADOGEN 240 1 | PHOS. .25@ | WV,VH,FP | WV,O,FP | WV,O,SP | N/A | N/A |
| | B | ADOGEN 240 1 | PHOS. .25@ | WV,O,SP | WV,O,MP | C,O,MP,FL | N/A | N/A |
| 80 | A | ADOGEN 240 3 | PHTHALIC .55@ | WV,O,MP,WP | WV,O,GP,WP | WV,O,MP,WP | N/A | N/A |
| | B | ADOGEN 240 3 | PHTHALIC .55@ | SV,O,GP,WP | SV,O,GP,WP | WV,O,GP,WP | N/A | N/A |
| 81 | A | ADOGEN 240 3 | OLEIC 6.0 | HV[10],O,VGP,CD | HV,O,EP,CD | HV,O,EP,CD | N/A | N/A |
| | B | ADOGEN 240 3 | OLEIC 7.0 | HV,O,VGP,CD | HV,O,EP,CD | HV,O,EP,CD | N/A | N/A |
| 82 | A | ADOGEN 240 1 | PHTHALIC .19@ | WV,H,FP,WP | WV,H,SP,WP | WV,C,O,MP,WP | N/A | N/A |
| | B | ADOGEN 240 1 | PHTHALIC .19@ | SV,H,FP,WP | WV,VH,MP,WP | WV,C,O,MP,WP | N/A | N/A |
| 83 | A | ADOGEN 240 1 | OLEIC 3.7 | WV,VH,FP,WP | WV,VH,VSP,WP | WV,H,O,SP,FL | N/A | N/A |
| | B | ADOGEN 240 1 | OLEIC 4.7 | SV,H,FP,WP | WV,VH,MP,WP | WV,C,O,MP,WP | N/A | N/A |
| 84[11] | A | ADOGEN N/A | N/A | WV,C | WV,C | WV,C | N/A | N/A |
| | B | ADOGEN N/A | N/A | WV,C | WV,C | WV,C | N/A | N/A |
| 85[12] | A | ADOGEN 240 3 | CITRIC 1.1@ | WV,O,SP | WV,C,O,SP,FL | C,O,SP,FL | N/A | N/A |
| | B | ADOGEN 240 3 | CITRIC 1.1@ | WV,O,MP | WV,C,O,SP,FL | WV,O,SP,FL | N/A | N/A |
| | A (S) | ADOGEN 240 3 | CITRIC 1.1@ | SV,O,VGP | MV,O,VGP | N/A | N/A | N/A |
| | B (S) | ADOGEN 240 3 | CITRIC 1.1@ | KV,O,VGP | MV,O,VGP | N/A | N/A | N/A |
| 86 | A | ADOGEN 240 3 | PHOS. .8@ | WV,O,FP | WV,C,O,SP | WV,C,O,SP | N/A | N/A |
| | B | ADOGEN 240 3 | PHOS. .8@ | WV,O,FP | WV,H,O,SP,FL | WV,C,O,SP | N/A | N/A |
| 87 | A | ADOGEN 240 1 | CITRIC .3@ | WV,O,FP | WV,H,O,SP | W,C,O,SP | N/A | N/A |
| | B | ADOGEN 240 1 | CITRIC .33@ | WV,O,FP | WV,H,O,SP | WV,H,O,SP | N/A | N/A |
| 88 | A | ADOGEN 240 1 | PHOS. .2@ | WV,O,SP | WV,C,O,SP,FL | WV,C,O,SP | N/A | N/A |
| | B | ADOGEN 240 1 | PHOS. .2@ | WV,O,SP | WV,H,O,MP,FL | KV,C,O,MP,FL | N/A | N/A |
| | A (S) | ADOGEN 240 1 | PHOS. .2@ | WV,O,SP | WV,H,O,MP | N/A | N/A | N/A |
| | B (S) | ADOGEN 240 1 | PHOS. .2@ | MV,O,GP | MV,O,GP | N/A | N/A | N/A |
| 89[13] | A | N/A | N/A @ | WV,C | WV,C | WV,C | N/A | N/A |
| | B | N/A | N/A @ | WV,C | WV,C | WV,C | N/A | N/A |
| 90[14] | A | ADOGEN 240 3 | CITRIC 1 | WV,O,FP | WV,C,VH,O,FP | WV,VH,O,SP | N/A | N/A |
| | B | ADOGEN 240 3 | CITRIC 1 | WV,O,FP | WV,C,O,MP | WV,C,O,MP | N/A | N/A |
| | A (S) | ADOGEN 240 3 | CITRIC 1 | SV,O,SP | SV,O,MP | N/A | N/A | N/A |
| | B (S) | ADOGEN 240 3 | CITRIC 1 | WV,O,FP | WV,O,VSP | N/A | N/A | N/A |
| 91 | A | ADOGEN 240 3 | PHOS. .7 | WV,O,FP | WV,C,O,FP | WV,H,O,VSP | WV,O,VSP | N/A |
| | B | ADOGEN 240 3 | PHOS. .7 | WV,O,SP | WV,C,O,SP | WV,C,O,SP | WV,O,SP | N/A |
| 92 | A | ADOGEN 240 1 | CITRIC .45 | WV,VH,FP | WV,VH,O,VSP | WV,H,O,FP,FL | (6 days) WV,O,VSP | N/A |
| | B | ADOGEN 240 1 | CITRIC .50 | WV,VH,FP | WV,VH,O,SP | WV,C,O,SP | WV,O,SP | N/A |
| 93 | A | ADOGEN 240 1 | PHOS. .32 | WV,VH,FP | WV,C,O,VSP | WV,H,O,FP,FL | (6 days) N/A | N/A |
| | B | ADOGEN 240 1 | PHOS. .37 | WV,VH,FP | WV,H,O,SP | WV,C,O,SP | N/A | N/A |
| | A(S) | ADOGEN 240 1 | PHOS. .32 | WV,O,FP | WV,C,O,VSP | N/A | N/A | N/A |
| | B (S) | ADOGEN 240 1 | PHOS. .37 | WV,O,GP | WV,O,GP | N/A | N/A | N/A |
| 94[15] | A | N/A | CITRIC .2 | WV,C | WV,C | WV,C | N/A | N/A |
| | B | N/A | CITRIC .225 | WV,C | WV,C | WV,C | N/A | N/A |
| 95[16] | A | ADOGEN 240 3 | CITRIC 1.2@ | WV,VH,FP | WV,VH,FP,Pr | WV,VH,FP | N/A | N/A |
| | B | ADOGEN 240 3 | CITRIC 1.2@ | WV,VH,FP | WV,VH,FP,Pr | WV,VH,FP | N/A | N/A |
| | A (S) | ADOGEN 240 3 | CITRIC 1.2@ | WV,VH,FP,Pr | WV,VH,FP,Pr | N/A | N/A | N/A |
| | B (S) | ADOGEN 240 3 | CITRIC 1.2@ | WV,VH,FP,Pr | WV,VH,FP,Pr | N/A | N/A | N/A |
| 96 | A | ADOGEN 240 3 | PHOS. 1@ | WV,H,FP | WV,H,O,FP | WV,VH,O,FP | N/A | |
| | B | ADOGEN 240 3 | PHOS. 1@ | WV,H,FP | WV,VH,O,VSP | WV,VH,O,FP | N/A | N/A |
| 97 | A | ADOGEN 240 1 | CITRIC .48@ | WV,H,FP | WV,C,FP | WV,C,FP | N/A | N/A |
| | B | ADOGEN 240 1 | CITRIC .48@ | WV,H,FP | WV,H,FP,Pr | WV,H,FP,Pr | N/A | N/A |
| 98 | A | ADOGEN 240 1 | PHOS. .4@ | WV,C,FP | WV,C,FP | WV,C,FP | N/A | N/A |
| | B | ADOGEN 240 1 | PHOS. .4 | WV,H,FP,Pr | WV,H,FP,Pr | WV,H,FP,Pr | N/A | N/A |
| 99[17] | A | N/A | CITRIC .2 | WV,C | WV,C | WV,C | N/A | N/A |
| | B | N/A | CITRIC .4 | WV,C | WV,C | WV,C | N/A | N/A |
| 100[18] | B | ADOGEN 240 3 | CITRIC .9@ | SV,O,GP,WP | SV,O,GP,WP | WV,O,GP,WP | N/A | N/A |
| | B (S) | ADOGEN 240 3 | CITRIC .9@ | SV,O,VGP | MV,O,VGP | N/A | N/A | N/A |

TABLE IV-continued

SHAMPOOS OPACIFIED WITH AN AMINE AND ACID

| Example | | Amine (%)[1] | Acid (%)[1] | Initial Appearance[2] | 24 hrs.[3] RT | 24 hrs.[3] 120° F. | Storage[4] RT | Storage[4] 120° F. |
|---|---|---|---|---|---|---|---|---|
| 101 | B | ADOGEN 240 3 | PHOS. .7@ | WV,O,GP,WP | WV,O,GP,WP | WV,O,GP,WP | N/A | N/A |
| 102 | B | ADOGEN 240 1 | CITRIC .3@ | WV,O,GP,WP | WV,O,GP,WP | WV,O,GP,WP | N/A | N/A |
| 103 | B | ADOGEN 240 1 | PHOS. .24@ | WV,O,GP,MP | WV,O,GP | WV,O,GP | N/A | N/A |
| 104 | A | ADOGEN 240 3 | CITRIC 2.7 | WV,O,GP,WP | WV,H,O,GP,WP | WV,H,O,GP,WP | N/A | N/A |
| 105[19] | A | N/A | CITRIC @ | WV,C | WV,C | WV,C | N/A | N/A |
|  | B | N/A | CITRIC .05@ | WV,C | WV,C | WV,C | N/A | N/A |
| 106 | C[20] | ADOGEN 240 3 | CITRIC 1@ | HV,O,GP | HV,O,GP | SV,O,GP | N/A | N/A |
|  | D | ADOGEN 240 3 | CITRIC 1@ | HV,O,GP | HV,O,GP | MV,O,GP | N/A | N/A |

[1] Active amount of amine and acid present in the composition, by weight; phos. is phosphoric acid;
[2] Appearance of the composition essentially immediately after manufacture;
[3] Appearance of the composition 24 hours after manufacture, both after storage at room temperature (about 75° F.) and at 120° F.;
[4] Appearance of the composition after storage for the indicated number of days, both at room temperature (about 75° F.) and at 120° F.;
[5] Examples 72 through 84 include 13% by weight ammonium lauryl sulfate;
[6] Compositions denoted A include only the anionic surfactant; Compositions denoted B further include cocamide DEA; Compositions denoted A(S) include an inorganic salt, e.g., sodium chloride, added to Composition A; and Compositions denoted B(S) include an inorganic salt added to composition B;
[7] The key for the appearance of the compositions is:
Rheology
WV = watery viscosity; SV = slight viscosity; MV = moderate viscosity; HV = high viscosity; CD = conditioner like rheology;
Appearance
O = opaque; SH = slightly hazy; H = hazy; C = clear; FL = flocculent; Pr = precipitate; WP = white particles of nonemulsified amine; FP = flat pearl; VSP = very slight pearl; SP = slight pearl; MP = moderate pearl; GP = good pearl; VGP = very good pearl; EP = excellent pearl; VELP = velvety pearl;
(Some compositions separated with the opaque layer being the top layer and the clear layer being the bottom layer. The hazy layer depends upon the presence of an opaque layer. For example: C,H,O,SP = clear bottom layer, hazy middle layer, and an opaque top layer with a slight pearl);
[8] N/A means not applicable;
[9] @ means sodium hydroxide was used to adjust the final pH of the composition;
[10] The high viscosity rating was by appearance, however, the viscosity is moderate by viscometer;
[11] The compositions of Example 84 are control samples, absent an opacifier of the present invention;
[12] Examples 85 through 89 include 13% by weight sodium laureth sulfate including an average of 2 moles of ethylene oxide;
[13] The compositions of Example 89 are control samples, absent an opacifier of the present invention;
[14] Examples 90 through 94 include 13% by weight sodium alpha-olefin sulfonate;
[15] The compositions of Example 94 are control samples, absent an opacifier of the prdsent invention;
[16] Examples 95 through 99 include 13% by weight sodium dodecylbenzene sulfonate;
[17] The compositions of Example 99 are control samples, absent an opacifier of the present invention;
[18] Examples 99 through 105 include 8.2% by weight ammonium lauryl sulfate and 4.8% by weight sodium laureth sulfate including an average of 2 moles of ethylene oxide, for 13% by weight total anionic surfactant;
[19] The compositions of Example 105 are control samples, absent an opacifier of the present invention; and
[20] The composition of Example 106 denoted C includes 6% by weight ammonium lauryl sulfate, 4.5% sodium lauryl sulfate and 10.5% ammonium laureth sulfate including an average of one mole of ethylene oxide; the composition denoted D is equivalent to the composition denoted C and further includes 2% by weight of a water-insoluble silicone hair conditioning composition.

From TABLE IV, the compositions Examples 84, 89, 94, 99 and 105 show that an anionic surfactant-based shampoo, absent an opacifier of the present invention is a clear, water-thin liquid. However, by including an opacifier of the present invention in the composition, the composition can have an initial appearance ranging from clear (Example 98(A)) to opaque (Example 72 (B)); with a pearlescence ranging from a flat pearl (Example 98(A)) to a velvety pearl (Example 73 (A(S)) ). In general, the velvety pearl was observed for opacifiers based on a primary amine. Therefore, different pearlescent effects can be achieved by a judicious selection of an amine of general structural formula (I). Although the compositions separated in some Examples, a judicious choice of a particular amine and acid, made in conjunction with the other ingredients present in the water-based composition, easily can be made by a person skilled in the art of shampoo formulation.

Therefore, the opacifier of the present invention provides a water-based composition that is esthetically pleasing and exhibits an ability to help suspend either a liquid or a particulate water-insoluble compound in the composition. The ability to help suspend the water-insoluble compound permits the incorporation of unexpectedly high amounts of silicones, hydrocarbons, antidandruff agents and other such water-insoluble agents or other hair treating compounds into a water-based shampoo composition. It is both surprising and unexpected for an opacifier of the present invention, including an amine of general structural formula (I) or (II) or (III), and a suitable acid, to effectively opacify or pearlize the water-based composition, to effectively resist phase separation, and to effectively help suspend a water-insoluble compound in the water-based composition to more effectively deliver the hair treating compound to the hair or scalp, while maintaining an acceptable foam level and exhibiting excellent physical and esthetic properties for consumer acceptance.

Obviously, many modifications and variations of the invention as hereinbefore set forth can be made without departing from the spirit and scope thereof and therefore only such limitations should be imposed as are indicated by the appended claims.

We claim:

1. A method of opacifying a surfactant-containing, water-based composition comprising the step of incorporating a sufficient amount of an opacifier into the water-based composition to reduce the transparency of the water-based composition, said opacifier consisting essentially of:

(a) about 1% to about 10% by weight of the water-based composition of an amine having the general structural formula,

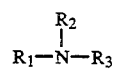

wherein $R_1$ is an alkyl group including at least 16 carbon atoms, and $R_2$ and $R_3$ are hydrogen, and wherein the amine is a solid compound at room temperature; and (b) a sufficient amount of acid such that essentially no solid particles of the amine are present in the composition and such that the composition has a pH of about 5.3 to 8.1, said acid selected from the group consisting of an inorganic mineral acid, an aliphatic carboxylic acid including up to about 22 carbon atoms, an aromatic carboxylic acid, and combinations thereof.

2. The method of claim 1, wherein the amine is present in an amount of about 1.5% to about 5% by weight of the water-based composition.

3. The method of claim 1, wherein the amine has a water solubility of 0.5 grams or less per 100 milliters of water.

4. The method of claim 1, wherein the amine is selected from the group consisting of $C_{20-22}$ amine, hydrogenated tallow amine, stearyl amine, tallow amine, hexadecylamine, octadecylamine, and combinations thereof.

5. The method of claim 1, wherein the inorganic mineral acid is selected from the group consisting of hydrochloric acid, sulfuric acid, nitric acid, phosphoric acid, and combinations thereof.

6. The method of claim 1, wherein the aliphatic carboxylic acid is a saturated aliphatic carboxylic acid including about 12 carbon atoms or less.

7. The method of claim 1, wherein the aromatic carboxylic acid is selected from the group consisting of benzoic acid, toluic acid, salicylic acid, phthalic acid, isophthalic acid, terephthalic acid, and combinations thereof.

8. The method of claim 1, wherein the acid is present in an amount of about 0.5% to about 5% by weight of the water-based composition.

9. The method of claim 1, wherein the water-based composition includes 0% to about 10% by weight of a water-insoluble hair treating compound.

10. The method of claim 9, wherein the water-insoluble hair treating compound is a conditioning agent, an antidandruff agent, or a combination thereof.

11. The method of claim 10, wherein the conditioning agent is selected from the group consisting of a silicone conditioning agent, a hydrocarbon conditioning agent, a water-insoluble fatty alcohol including about 12 to about 22 carbon atoms, a water-insoluble fatty ester including about 9 to about 34 carbon atoms, and combinations thereof.

12. The method of claim 9, wherein the antidandruff agent is selected from the group consisting of salicylic acid, elemental sulfur, selenium sulfide, zinc pyrithione, an azole antimycotic, a water-insoluble 1-hydroxy pyridone, undecylenic acid, and combinations thereof.

* * * * *

UNITED STATES PATENT AND TRADEMARK OFFICE
CERTIFICATE OF CORRECTION

PATENT NO. : 5,384,114

DATED : January 24, 1995

INVENTOR(S) : Teresa J. Dowell et al.

It is certified that error appears in the above-identified patent and that said Letters Patent is hereby corrected as shown below:

Column 1, line 15, "waterinsoluble" should be -- water-insoluble --

Column 1, line 24, "$R^2$" should be -- $R_2$ --

Column 1, line 52, delete second occurrence of "insoluble"

Column 3, line 30, "$R^2$" should be -- $R_2$ --

Column 3, line 44, "$R_8$" should be -- $R_5$ --

Column 4, line 1, between "and" and "improved" insert -- imparts --

Column 4, line 35, formula (I), "$R^2$" should be -- $R_2$ --

Column 5, line 6, formula (I), "$R^2$" should be -- $R_2$ --

Column 5, line 56, formula (I), "$R^2$" should be -- $R_2$ --

Column 6, line 26, delete "$R_9$"

Column 7, lines 50, 51, "stearamidoethyldimethylamine" should be -- stearamidoethyl dimethylamine --

Column 12, line 10, between "20°C," and "700,000" insert -- *e.g.* --

Column 12, line 27, the sentence beginning with "An example..." should start a new paragraph Column 13, line 61, "$C_{22}$carboxylic" should be -- $C_{12}$ carboxylic --

UNITED STATES PATENT AND TRADEMARK OFFICE
CERTIFICATE OF CORRECTION

PATENT NO. : 5,384,114

DATED : January 24, 1995

INVENTOR(S) : Teresa J. Dowell et al.

It is certified that error appears in the above-identified patent and that said Letters Patent is hereby corrected as shown below:

Column 14, line 50, "vinylpyrrolidone/ dime-" should be
-- vinylpyrrolidone/dime- --

Column 19, line 66, "for." should be --for--

Columns 23, 24, Table II, line beginning with "42," "ADOGEN 140 (34%)" should be
-- ADOGEN 140 (3%) --

Columns 23, 24, Table II, line beginning with "43," "ADOGEN 140 (2.51%)" should be
-- ADOGEN 140 (2.5%) --

Columns 23, 24, Table II, line beginning with "55," column headed "Stability," "pearlescence" should be moved to column headed "Appearance" to read
--Good pearlescence--

Columns 23, 24, Table II, line beginning with "56," column headed "Stability," "pearlescence" should be moved to column headed "Appearance" to read
--Good pearlescence--

Columns 23, 24, Table II, line beginning with "57," column headed "Stability," "pearlescence" should be moved to column headed "Appearance" to read
--Good pearlescence--

UNITED STATES PATENT AND TRADEMARK OFFICE
CERTIFICATE OF CORRECTION

PATENT NO. : 5,384,114

DATED : January 24, 1995

INVENTOR(S) : Teresa J. Dowell et al.

It is certified that error appears in the above-identified patent and that said Letters Patent is hereby corrected as shown below:

Columns 23, 24, Table II, line beginning with "58," column headed "Stability," "pearlescence" should be moved to column headed "Appearance" to read
--Good pearlescence--

Columns 23, 24, Table II, line beginning with "59," column headed "Stability," "pearlescence" should be moved to column headed "Appearance" to read
--Good pearlescence--

Columns 23, 24, Table II, line beginning with "60," column headed "Stability," "pearlescence" should be moved to column headed "Appearance" to read
--Poor pearlescence--

Columns 25, 26, Table IV, line beginning with "72 [5)]," column headed "Amine (%)[1]," "A" should be --A [6)]--

Columns 27, 28, Table IV-continued, line beginning with "76," column headed "RT," "VV,O,SP" should be --WV,O,SP--

Columns 27, 28, Table IV-continued, section beginning with "77," column headed "Acid (%)," "PHOS. .76" should be --PHOS. .7@--

Columns 27, 28, Table IV-continued, section beginning with "85," fourth line, column headed "Initial Appearance," "KV,O,VGP" should be --MV,O,VGP--

Columns 27, 28, Table IV-continued, section beginning with "87," line 1, column headed "Acid (%)," "CITRIC .3@" should be --CITRIC .33@--

UNITED STATES PATENT AND TRADEMARK OFFICE
CERTIFICATE OF CORRECTION

PATENT NO. : 5,384,114

DATED : January 24, 1995

INVENTOR(S) : Teresa J. Dowell et al.

It is certified that error appears in the above-identified patent and that said Letters Patent is hereby corrected as shown below:

Columns 27, 28, Table IV-continued, section beginning with "96," line 1, last column, insert --N/A--

Columns 27, 28, Table IV-continued, section beginning with "98," line 2, column headed "Acid (%)," "PHOS. .4" should be --PHOS. .4@--

Columns 29, 30, Table IV-continued, section beginning with "103," column headed "Initial Appearance," "WV,O,GP,MP" should be --WV,O,MP--

Columns 29, 30, footnote No. 15, "prdsent" should be --present--

Signed and Sealed this

Second Day of May, 1995

BRUCE LEHMAN

*Attest:*

*Attesting Officer*  *Commissioner of Patents and Trademarks*